(12) United States Patent
Güder et al.

(10) Patent No.: US 10,712,337 B2
(45) Date of Patent: Jul. 14, 2020

(54) DETECTING GASES AND RESPIRATION BY THE CONDUCTIVITY OF WATER WITHIN A POROUS SUBSTRATE SENSOR

(71) Applicant: President and Fellows of Harvard College, Cambridge, MA (US)

(72) Inventors: Firat Güder, Watertown, MA (US); Bobak Mosadegh, New York, NY (US); Alar Ainla, Somerville, MA (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 328 days.

(21) Appl. No.: 15/521,190

(22) PCT Filed: Oct. 22, 2015

(86) PCT No.: PCT/US2015/056971
§ 371 (c)(1),
(2) Date: Apr. 21, 2017

(87) PCT Pub. No.: WO2016/065180
PCT Pub. Date: Apr. 28, 2016

(65) Prior Publication Data
US 2017/0356899 A1    Dec. 14, 2017

Related U.S. Application Data

(60) Provisional application No. 62/067,291, filed on Oct. 22, 2014.

(51) Int. Cl.
*A61B 5/02* (2006.01)
*G01N 33/497* (2006.01)
*A61B 5/08* (2006.01)
*G01N 27/12* (2006.01)
*A61B 5/00* (2006.01)

(52) U.S. Cl.
CPC ......... *G01N 33/497* (2013.01); *A61B 5/0022* (2013.01); *A61B 5/082* (2013.01);
(Continued)

(58) Field of Classification Search
CPC ...... G01N 27/12; G01N 27/121; A61B 5/082; A61B 5/0826; A61B 5/0816
See application file for complete search history.

(56) References Cited

U.S. PATENT DOCUMENTS 7,992,426 B2 *   8/2011   Fleischer ........... G01N 27/4143
                                                          73/31.06
2009/0261987 A1  10/2009  Sun
(Continued)

OTHER PUBLICATIONS

Han, J.-W., et al., "Carbon Nanotube Based Humidity Sensor on Cellulose Paper," The Journal of Physical Chemistry C, vol. 116, No. 41, pp. 22094-22097 (Oct. 18, 2012).
(Continued)

*Primary Examiner* — Christian Jang
(74) *Attorney, Agent, or Firm* — Wilmer Cutler Pickering Hale and Dorr LLP

(57) ABSTRACT

A method of and system for detecting a gas or vapor includes providing a sensor comprising an electrode pair in electrical contact with a layer of porous material, the porous material layer having water adsorbed on its surface; contacting the sensor with a gas or vapor sample to be analysed; applying a voltage across the electrode pair of the sensor; and measuring a response, the response correlating to the presence of a target gas or vapor.

18 Claims, 21 Drawing Sheets

(52) U.S. Cl.
CPC .......... *A61B 5/0816* (2013.01); *A61B 5/0826* (2013.01); *G01N 27/12* (2013.01); *G01N 27/121* (2013.01); *G01N 2033/4975* (2013.01)

(56) References Cited

U.S. PATENT DOCUMENTS

2010/0175699 A1* 7/2010 Varney .................. A61B 5/0816
  128/204.23
2011/0290003 A1 12/2011 Liu et al.

OTHER PUBLICATIONS

Huang, L., et al., "A novel paper-based flexible ammonia gas sensor via silver and SWNT-PABS inkjet printing," Sensors and Actuators B: Chemical, vol. 197, pp. 308-313 (Jul. 5, 2014).

International Search Report and Written Opinion issued by the U.S. Patent and Trademark Office for the International Application No. PCT/US15/56971 dated Jan. 14, 2016 (13 pages).

Kim, J.-H., et al., "Disposable chemical sensors and biosensors made on cellulose paper," Nanotechnology, vol. 25, pp. 1-7 (Feb. 12, 2014).

Liu, H., et al., "Physically Flexible, Rapid-Response Gas Sensor Based on Colloidal Quantum Dot Solids," Advanced Materials, vol. 26, Issue 17, pp. 2718-2724 (May 7, 2014).

Mirica, K. A., et al., "Rapid prototyping of carbon-based chemiresistive gas sensors on paper," Pnas, pp. E3265-E3270 (published online Aug. 13, 2013).

Timmer, B., et al., "Ammonia sensors and their applications—a review," Sensors and Actuators B, vol. 107, pp. 666-677 (Jun. 2005).

Yang, B., et al., "Compliant and low-cost humidity nanosensors using nanoporous polymer membranes," Sensors and Actuators B, vol. 114, Issue 1, pp. 254-262 (Mar. 30, 2006).

* cited by examiner

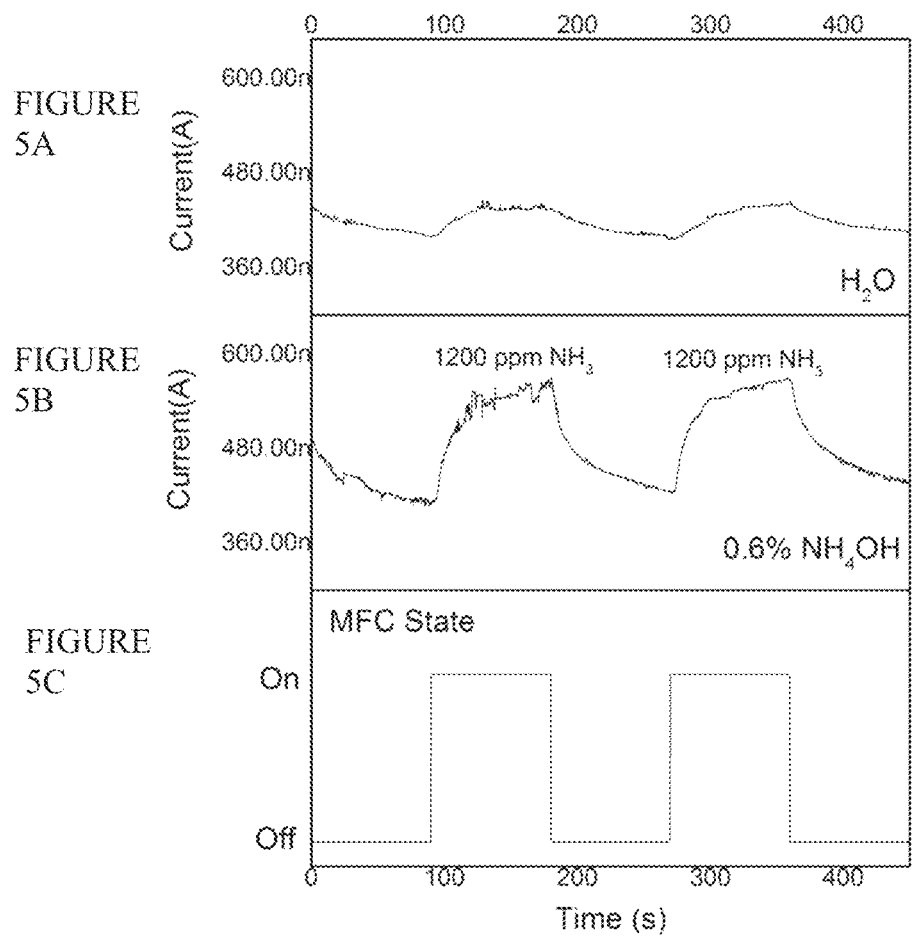

FIGURE 15A
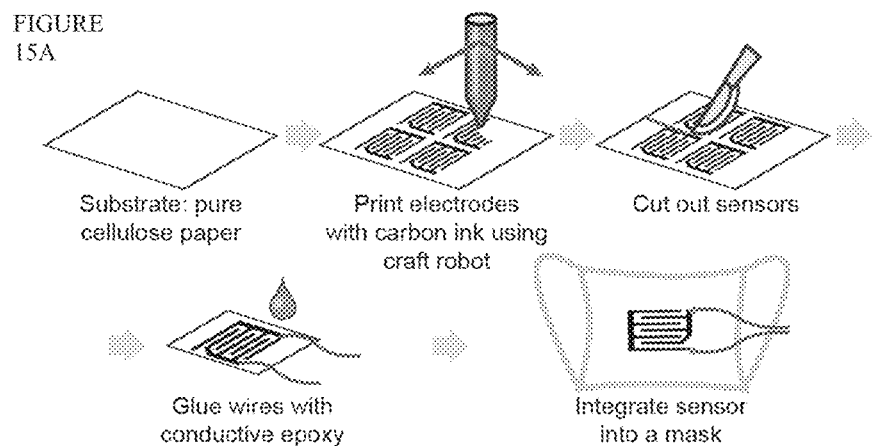
FIGURE 15B
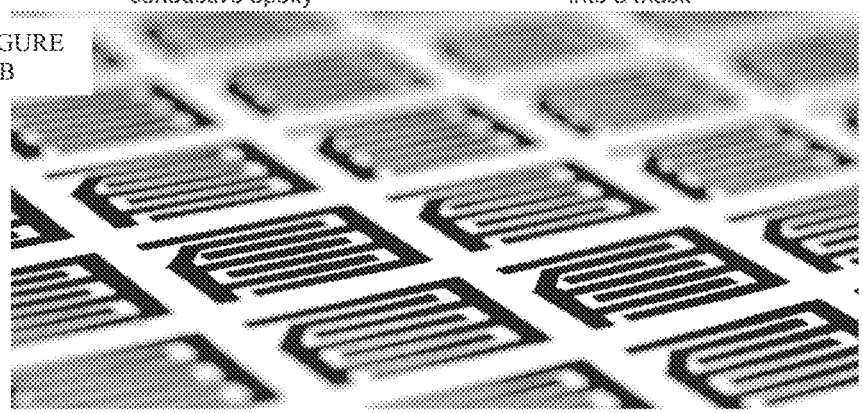
FIGURE 15C
 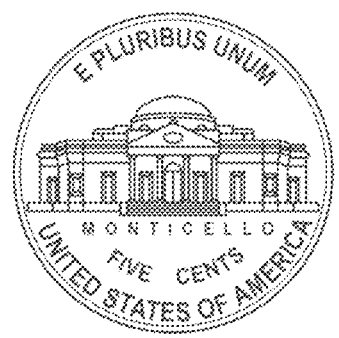

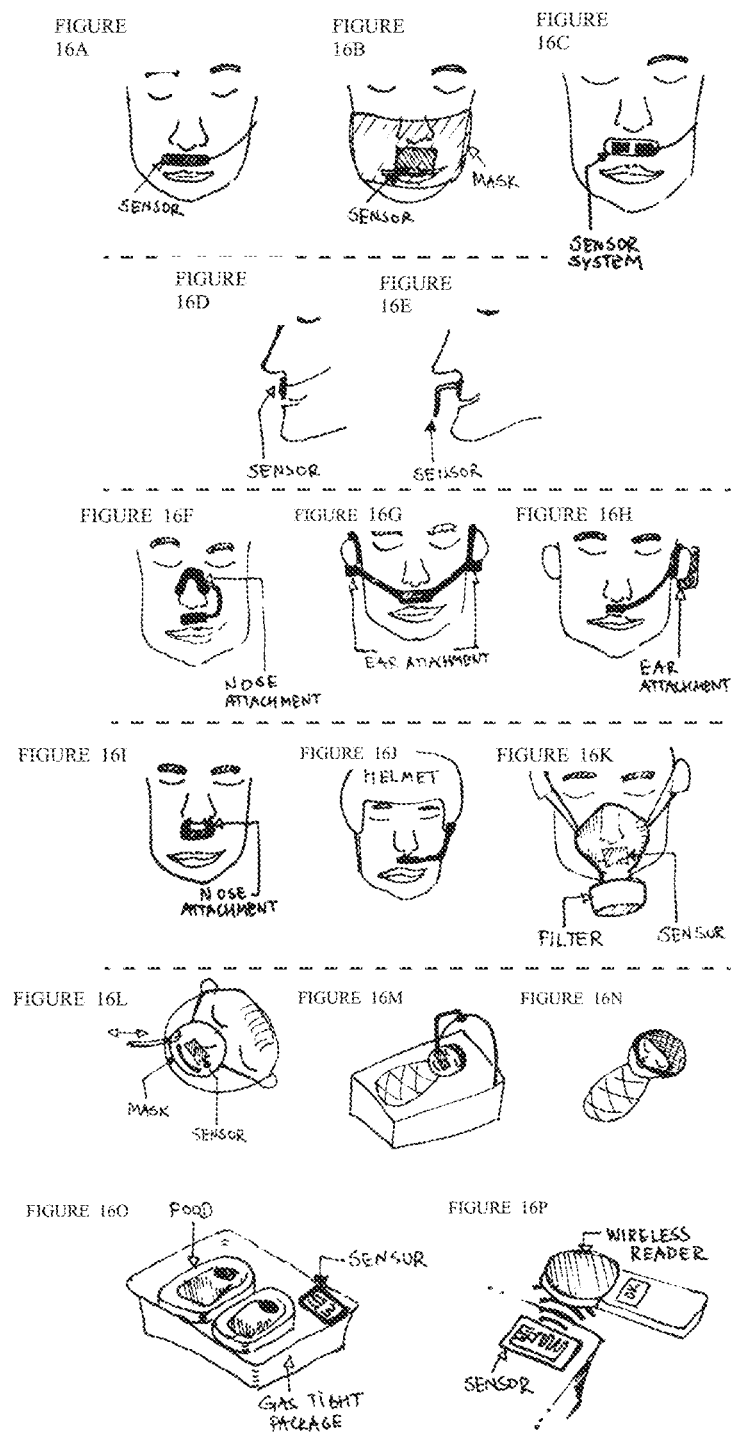

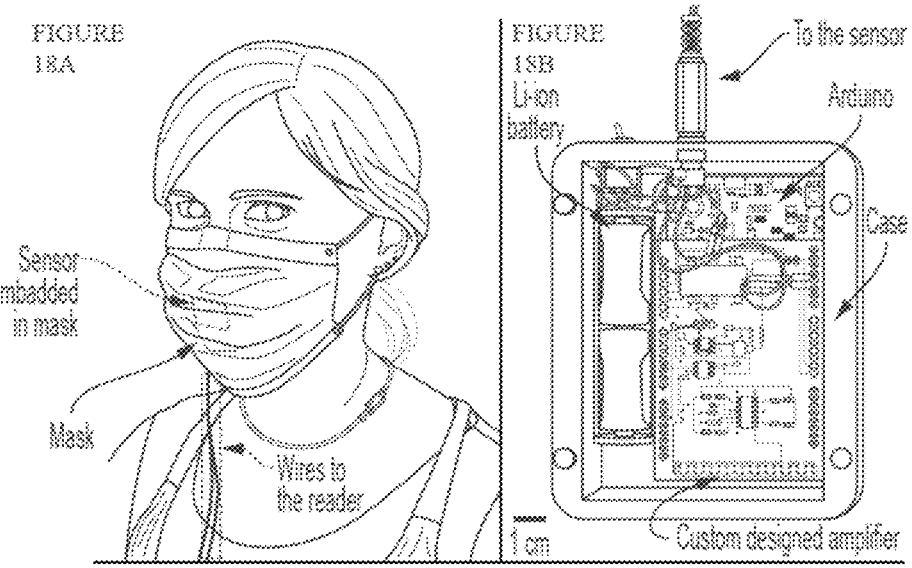
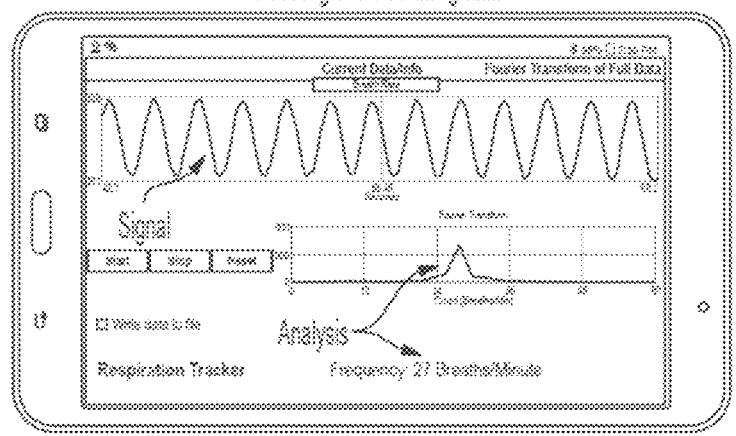
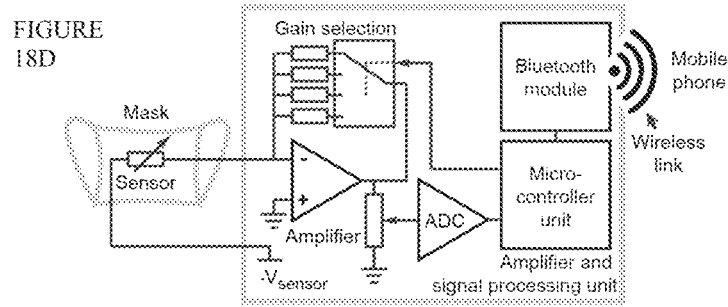

DETECTING GASES AND RESPIRATION BY THE CONDUCTIVITY OF WATER WITHIN A POROUS SUBSTRATE SENSOR

RELATED APPLICATIONS

This application is a national stage application of International Application No. PCT/US2015/56971 filed Oct. 22, 2015, which claims priority to U.S. Provisional Application Ser. No. 62/067,291, filed Oct. 22, 2014, the contents of which are incorporated in their entirety by reference.

INCORPORATION BY REFERENCE

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described herein.

TECHNICAL FIELD

This technology relates generally to gas detection. In particular, this invention relates to compliant sensors fabricated from low cost materials.

BACKGROUND

Sensors for gases are becoming an integral part of our technology-dependent lives, such as in cars (performance and emissions control), buildings (air quality management), factories (process control and leak detection) and food processing and packaging (freshness and ripeness control).

Medical diagnostics is yet another emerging area that requires low-cost and accurate detection and quantification of gaseous analytes. The presence of various gases (e.g., acetone, ammonia) at certain concentrations in breath, for instance, is linked to certain health conditions such as diabetes and failure of the kidney and liver.

Rapid and low-cost development of sensors of gas remains a major challenge for several reasons: i) use of expensive and unscalable detection methods (i.e. infrared gas sensors), ii) use of complex fabrication procedures (i.e. vapor phase grown ceramic thin films), iii) dependence on high temperatures for detection (e.g. metal-oxide sensors), iv) offer low level of selectivity, v) use of rigid/non-flexible materials, and vi) require frequent calibration for accurate readings.

Previous examples of paper-based sensors of gases involve the integration of carbon nanotubes, quantum dots or other forms of nanostructures on paper. These examples use the nanostructures as the active sensing material and the paper itself is only a scaffold.

Breathing is one of the primary vital signs used to diagnose the health status of patients; it is related to many common disorders and diseases, ranging from pulmonary and cardiovascular diseases to sleep-related disorders. Current methods of monitoring breathing require cumbersome, inconvenient and often expensive devices; In prior methods, the breathing patterns are recorded via insertion of a nasal cannula into the patient's nose. The cannula is attached to a pressure sensor, which measures the breathing of the patient. When the patient breathes through the mouth, however, this method of detection fails to sense the changes in breathing giving rise to false diagnosis. To mitigate this issue, other health parameters such as chest motion and blood oxygen levels are tracked. This requirement sets practical limitations on the frequency and duration of measurements. To circumvent the complications of on-site clinical testing, at-home testing of sleep apnea is being developed. For example, a cell phone assisted take-home sleep test included an array of sensors that correlated the blood oxygen levels and heart rate with occurrence of reduced or paused air flow during sleep. Although the overall system was satisfactory, the device was bulky (required 2xAAA batteries) and consisted of expensive components, increasing the cost of ownership.

Sleep apnea is a disorder in which the flow of air into and out of the lungs is fully or partially obstructed for at least 10 seconds continuously. This paused or shallow breathing is linked to a variety of health problems, including but not limited to cardiovascular diseases, stroke, and diabetes.

Take-home sleep apnea tests are available, such as AccuSom by NovaSom and WatchPAT. Current methods of detection hinder proper diagnosis of this condition because of two reasons: i) diagnosis is primarily done in clinical settings which is time-consuming and difficult for most patients to participate in, and ii) current take-home tests are too expensive and cumbersome to operate for patients to adopt these technologies. An effective solution to take-home sleep apnea testing still does not exist.

The most common strategy for diagnosis is to perform a sleep study at a clinical site. These studies often require an overnight stay and supervision of specialized personnel. From the initial discussions with the physician to the diagnosis from a complete sleep study can take up to six weeks. The inconvenience of these studies is the primary reason preventing people who suspect having sleep apnea from getting diagnosed.

SUMMARY

In one aspect, gas sensors that operate at room-temperature are described. The sensors are built on hygroscopic porous substrates that are able to attract and adsorb water from the environment. These and other aspects and embodiments of the disclosure are illustrated and described below.

In another aspect, a sensor that can accurately measure respiration, diagnose sleep apnea or monitor other respiration conditions by exploiting the changes in conductivity of paper when breathed upon are described.

In one aspect, a method of detecting a gas or vapor includes providing a sensor comprising an electrode pair in electrical contact with a layer of porous material, the porous material having water adsorbed on its surface; contacting the sensor with a gas or vapor sample to be analysed; applying a voltage across the electrode pair of the sensor; and measuring a response, in which the response correlates to the presence of a target gas.

In one or more embodiments, the porous material layer is a fiber-based layer, or a hydroscopic layer, or a cellulose-based layer.

In one or more embodiments, the fiber-based layer is selected from the group of woven textiles or fabrics, non-woven textiles or fabrics, non-woven meshes and paper.

In one or more embodiments, the porous material is an inorganic oxide.

In one or more embodiments, the electrode pair are aligningly disposed on opposing surfaces of the porous layer, or the electrode pair are spaced apart on the same side of the porous layer.

In one or more embodiments, the electrodes are disposed on the same side of the porous layer.

In any of the preceding embodiments, the response includes one or more of current, electrical resistance, voltage, or conductance.

In any of the preceding embodiments, the magnitude of the response correlates to a concentration of the target gas or vapor.

In any of the preceding embodiments, the porous fiber-based layer comprises cellulose-based paper.

In any of the preceding embodiments, the target gas includes a strong or weak acid or base.

In any of the preceding embodiments, the target gas includes a water soluble organic compound.

In any of the preceding embodiments, the target gas includes water, and for example, the response is an increase in current, indicating an increase in the adsorbed water in the sensor.

In any of the preceding embodiments, the response is an increase in current, indicating an increase in ionic conductivity in the adsorbed water in the sensor, or the response is a decrease in current, indicating a decrease in ionic conductivity of the adsorbed water in the sensor.

In any of the preceding embodiments, the sensor further includes an amplifying agent, and for example, the amplifying agent is compound capable of being ionized by the target gas.

In any of the preceding embodiments, the target gas is ammonia and the amplifying agent is zinc oxide.

In any of the preceding embodiments, the amplifying agent is a salt that is soluble in the adsorbed water of the sensor.

In any of the preceding embodiments, the sensor further includes a damping agent, the damping agent selected to reduce a response from a non-selected gas.

In any of the preceding embodiments, the sensor further includes an input for the relative humidity in the vicinity of the sensor, and for example, the response is adjusted to take account of the relative humidity input.

In any of the preceding embodiments, the sensor further includes a sensitizing agent that increases the response sensitivity to changes in concentration of the target gas or vapor, and for example, the sensitizing agent is a water soluble salt.

In one aspect, a sensor for detecting a target gas includes an electrode pair in electrical contact with a layer of porous material, in which the layer of porous material has water adsorbed on its surface; electrical contacts capable of connection with a voltage source for applying a bias across the electrode pair.

In one or more embodiments, the sensor a further includes an amplification agent, and/or a damping agent, and/or a sensitizing agent as described above in preceding embodiments.

In one or more embodiments, the porous material a fiber-based layer, or a hydroscopic layer, or a cellulose-based layer, and the fiber-based layer can be selected from the group of woven textiles or fabrics, non-woven textiles or fabrics, non-woven meshes and paper, and the porous material can be an inorganic oxide or a cellulose-based paper as described above in preceding embodiments.

In one or more embodiments, the sensor a further includes a microcontroller, the microcontroller having instructions and hardware for executing one or more of the following tasks: modifying applied bias, amplifying signals, digitizing signals, transmitting and receiving data over a wireless communication system.

In one or more embodiments, the sensor a further includes a wireless communication system.

In one or more embodiments, the sensor a further includes an voltage source.

In one aspect, a method of detecting respiration of a patient includes providing a sensor comprising an electrode pair in contact with a layer of porous material, the porous material capable of adsorbing and desorbing water as a function of relative humidity; positioning the sensor in the vicinity of the mouth and/or nose of a patient; and monitoring the change in water content of the sensor over time, wherein the increase and decrease in water content is correlated to exhalation and inhalation, respectively.

In one or more embodiments, the method employs multiple sensors, located in the vicinity of one or more of the nostrils and mouth.

In one or more embodiments, the method detects a respiratory condition such as apnea, hypopnea and respiratory arrhythmia.

In any of the preceding embodiments, the change in water content is determined by applying a voltage across the electrode pair of the sensor, and measuring a response, said response correlating to the level of adsorbed water.

In any of the preceding embodiments, the response is an increase in current, indicating an increase in the adsorbed water in the sensor.

In any of the preceding embodiments, the response includes one or more of current, electrical resistance, voltage, or conductance.

In any of the preceding embodiments, the response is wirelessly transmitted from the sensor to a remote location.

In any of the preceding embodiments, a microcontroller is used to process the response of the sensor to generate data representative of said change of water content over time in an exhaled gas stream.

In any of the preceding embodiments, the increase and decrease in water content is used to generate data representative of breathing rate.

In any of the preceding embodiments, the increase and decrease in water content is used to generate data representative of breathing depth.

In one aspect, a respiration monitor includes a support capable of being positioned in the vicinity of the mouth and/or nose of a patient; and a sensor comprising an electrode pair in electrical contact with a layer of porous material capable of adsorbing and desorbing water as a function of relative humidity, said sensor attached to the support and located so as to be in the pathway of patient inhalation and exhalation.

In one or more embodiments, the respiration monitor further includes a voltage source configured to apply a voltage across the electrode pair, and for example, the voltage source is a battery.

In one or more embodiments, the respiration monitor further includes a microcontroller for measuring a change in one or more of current, electrical resistance, voltage, or conductance.

In one or more embodiments, the respiration monitor further includes a wireless transmitter for transmission of meter data to a remote location.

In one or more embodiments, the respiration monitor further includes a sensitizing agent.

BRIEF DESCRIPTION OF THE DRAWINGS

The invention is described with reference to the following figures, which are presented for the purpose of illustration only and are not intended to be limiting.

In the Drawings:

FIG. 5 is a plot of an output of the sensor of untreated paper when exposed to water only (FIG. 5A) and after $NH_4OH$ is added to the paper substrate (FIG. 5B). FIG. 5C shows the gas pulse timing (flow control, FC) used to generate the data for plots on FIG. 5A and 5B.

FIGS. 10A-F are schematic illustrations for various electrode configurations used in the sensor according to one or more embodiments, in which FIG. 10A shows electrodes on opposite sides of the porous substrate; FIG. 10B shows electrodes on the same sides of the porous substrate; FIG. 10C is a schematic illustration of a four point measurement used to measure current in the sensor according to one or more embodiments; FIG. 10D is a schematic of an equivalent circuit of a sensor, where EC denotes electrochemical process, according to one or more embodiments; FIG. 10E shows a LC resonant circuit containing a sensor (S) affecting the Q factor (damping) or resonance frequency of the resonant circuit according to one or more embodiments; and FIG. 10F shows plots of current vs. frequency to show a change in resonance frequency or Q factor according to one or more embodiments.

FIG. 15A is a schematic illustration of an exemplary fabrication of digitally printed paper sensors with graphite ink; according to one or more embodiments; FIG. 15B is an image of an array of digitally printed sensors according to one or more embodiments; and FIG. 15C is an enlarged view of a single interdigitated electrode pair according to one or more embodiments.

FIG. 16A-P are schematic illustrations of respiration sensors according to one or more embodiments.

FIG. 18A is a photograph of a facemask with the embedded paper-based sensor, according to one or more embodiments; FIG. 18B is a photograph of the data acquisition electronics with Li-ion batteries, Arduino microcontroller board, a Bluetooth module, a voltage source (battery), custom designed amplifier board, and 3D printed casing; FIG. 18C is photograph of tablet computer running the Android app, which can display and analyse the incoming data stream from the data acquisition electronics; and FIG. 18D is a simplified circuit diagram of the electronics.

DETAILED DESCRIPTION

Gas or Vapor Sensor

In one aspect, a sensor using a porous substrate having an adsorbed layer of water for detecting gases is provided. For ease of reference, the gas sensor is described with reference to paper as the substrate. However the principles described herein are readily applied to any porous hygroscopic substrate.

Figure 1:
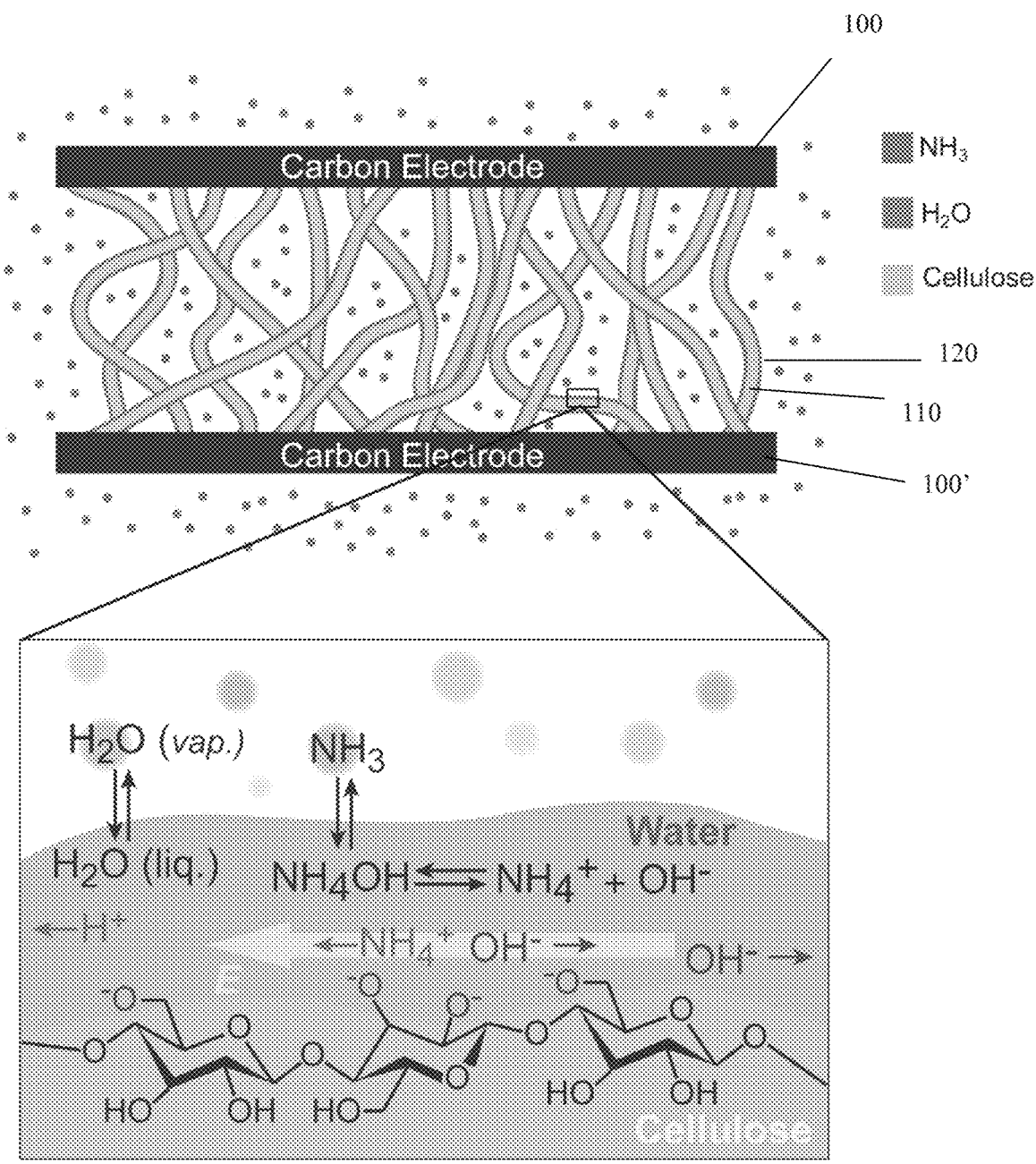
FIG. 1 a schematic illustration of the mechanism sensing of the gas sensor according to one or more embodiments, in which the porous layer contains a layer of water on its surface so that the layer of water acts as an electrolyte for ionic transport and the concentration of ions is determined by measuring the conductivity between two electrodes.

FIG. 1 is a schematic illustration of a cellulosic gas detector according to one or more embodiments. The device includes a pair of electrodes 100, 100' with a porous layer 110 disposed in between. Electrodes are shown on opposing sides of the porous layer, however, it is contemplated that the electrodes can be disposed on the same side of the paper layer. See, e.g., FIG. 15. When exposed to ambient conditions, the device is exposed to atmospheric water, as well as any gas to be detected (exemplified here with ammonia ($NH_3$)). A thin layer of adsorbed water 120 forms in and/or on the porous layer. Water is in equilibrium conditions between the free water vapor and adsorbed water, as shown in the exploded view in FIG. 1. $NH_3$ is a polar gas that dissolves in water and forms $NH^{4+}$ and $OH^-$ ions. These ions contribute to the overall ionic conduction of the adsorbed water on the cellulose fibers of the paper. The exploded view in FIG. 1 also shows how $NH_3$ interacts with the moist fibers of the porous layer. On application of a voltage, current is induced in the layer due to the ionic conductivity of the water layer. The current is proportional to the ionic content of the water layer, which is perturbed when exposed to ambient gases. Thus changes in the current are indications of changes in the ambient gas composition.

In one or more embodiments, the electrodes are disposed in close proximity on one side of the substrate. In some embodiments, the electrodes are interdigitated to increase the area of the area of the electrode and the signal to noise ratio. See, FIG. 15. This design also allows rapid access of humidity and target gases and vapors to the paper. In other embodiments, electrodes are disposed on opposite sides of the paper detector, for example, by printing electrodes on both sides of a single sheet of paper. Contacts can be provided for connection to an external voltage source.

The moisture within a sheet of paper offers a unique method for sensing concentrations of gas since the ionic conductance of the paper is proportional to the concentration of ionic species dissolved within the adsorbed water. Gases capable of detection include those that are water soluble. As the gases interact with the adsorbed water, the ion concentration of the adsorbed water changes, which can be recorded as current. In some embodiments, the dissolved gases are ionized in the water layer adsorbed on the porous layer and increase ionic conductivity. In other embodiments, the gases are solvated in the adsorbed water layer without ionization and decrease ionic conductivity. Exemplary gases that can be detected include gases having strong to mild acidic or basic properties (e.g., $NH_3$, HCl, $SO_2$, nitrogen oxide ($NO_x$), halides) and volatile organic compounds having solubility in water (e.g., acetone and ethanol). In other embodiments, gases or vapors that have poor solubility in water, or that are not sufficiently acidic or basis, such as $CO_2$ by way of example, can still detected by including reagents in the porous layer that interact with the target gas and convert it into an ionized species. For example, the enzyme carbonicanhydrase converts $CO_2$ into $HCO^{3-}$.

By applying a bias between the two electrodes, the ionic conductance of the paper can be quantified based on the measured current. The bias can be direct current (DC), alternating current (AC) or pulsed signal. A change in the measured current provides an indication of gas presence and the magnitude is a measure of the concentration of a gas.

The substrate can be any porous material that is hygroscopic. Exemplary materials include fiber-based materials, such as woven textiles, non-woven meshes, and woven and non-woven fabrics and textiles. Cellulose-based materials are particularly useful. Cellulose-based substrates such as certain textiles and fabrics, e.g., cotton fabrics, and paper are exemplary cellulose-based substrate. Other exemplary substrates include porous inorganic materials, such as inorganic oxides, such as alumina and silica In other embodiments, a porous substrate can be coated with an oxide layer to create a hygroscopic substrate.

In one or more embodiments, the substrate is paper, and in particular, cellulose-based paper. Cellulose paper has a very high affinity to ambient water. At a relative humidity of 70%, the moisture content in cellulose paper can be as high as 10% by weight. In addition to its ability to absorb high amounts of water from air, cellulose paper has several other advantages as a sensor for gases: i) cellulose paper is inherently porous, a feature that allows gases to penetrate and interact easily with the bulk of the material in the sensor, ii) cellulose paper has a high surface area (over 100 $m^2$/g) so the sensitivity of the sensor is greater than thin films that operate using the same mechanism, iii) cellulose paper is chemically inert to most gases including highly corrosive species; and "iv) cellulose fibers themselves are not electronically conductive (electronic insulator), therefore the conductivity of the sensor depends solely on the ionic conductivity in the absorbed water layer. In one or more embodiments, the paper is thick enough to prevent printed contacts from short circuiting.

Electrodes can be deposited on the substrate using a variety of methods. In one embodiment, electrodes can be prepared separately and pressed conformally against the porous substrate. Aluminum film and copper sheers are examples of materials available in free standing thin films that can be used as electrodes. In other embodiments, an electrode pair can be laminated on the porous substrate. The laminated material can be a thin metal sheet or foil such as aluminium or gold. In other embodiments, the electrode pair can be printed on the porous material. The printing material can be any of the following non-limiting examples: carbon inks, nanofiber inks, suspended metal particle inks, reactive inks (e.g., inks which are not conductive themselves (e.g., dissolved metal complex), but which upon printing through the process of reacting with substrate, decomposing thermally or reacting with some other substance applied subsequently are turned into a conductive materials (through chemical reaction) and conductive polymer inks The inks can be printed using conventional and low cost methods such as screen-printing, stencil printing, plotting, and roll-to-roll printing. In other embodiments, the electrodes can be made using gas phase deposition techniques such as physical or chemical vapor deposition, or sputtering. Deposition methods can apply the electrodes to the porous substrate surface, or the electrodes can penetrate to the interior of the porous substrate.

In one or more embodiments, the electrodes are located on the same side of the substrate. In other embodiments, the electrodes are located on opposite sides of the substrate. The electrodes can be designed to have large surface area and to permit environmental vapor access to the underlying substrate.

Figure 2A:
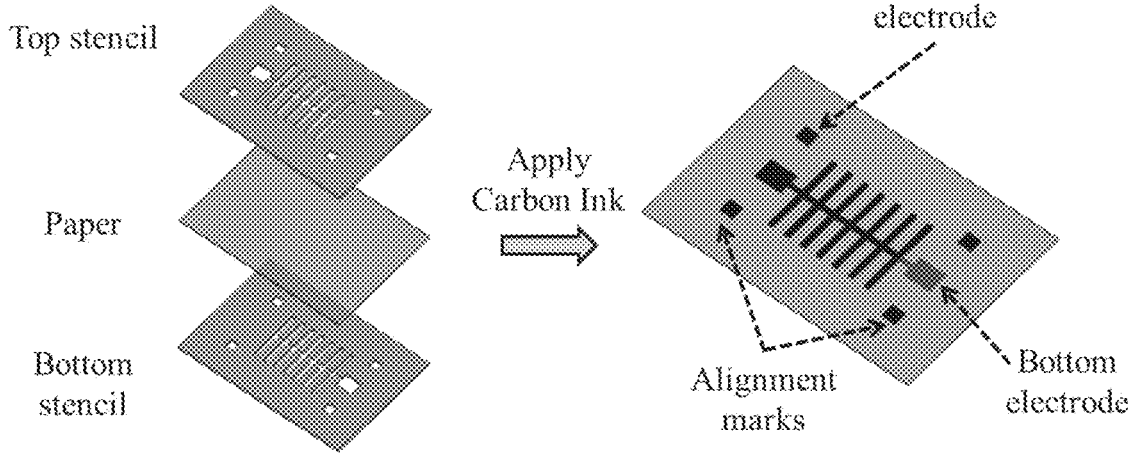
FIG. 2A is a schematic illustration of fabrication procedure of the paper-based gas sensors and FIG. 2B is a photograph of an actual device (the light source is behind the device, showing the aligned electrodes at both the front and back of the paper) and a magnified photograph of the device cross-section.

The devices can be prepared using any available method. In one or more embodiments, electrodes are printed onto paper with current printing technologies (e.g., screen printing). Printing offers a unique possibility for the rapid fabrication of low-cost, low-power, and flexible sensors with tailor-made properties. FIG. 2A is a schematic illustration of the fabrication of a paper-based gas sensor according to one or more embodiments, in which a cellulosic substrate is sandwiched between two carbon electrodes. Low-cost and easy-to-apply graphite ink is silk-screened onto a first side of the cellulose paper to form chemically inert carbon electrodes. Once dried and optionally heated, the paper is flipped and the counter electrode is printed on the opposite side. Printing allows fabrication of multiple devices on the same substrate; the electrodes can be designed to span a large surface area of the paper, to increase sensitivity. Contacts for connection to a voltage source can also be directly printed onto the substrate. The method produces well-aligned electrodes on the front and back of the paper, as shown in the photograph in FIG. 2B. Both the top electrode and the bottom electrode are visible and the overlap/alignment of the two electrodes is high, as shown in the cross-section of the sensor.

In other embodiments, the electrodes can be on the same side of the porous substrate, as is shown in FIGS. 15A-15C. As shown in FIG. 15A, an electrode is fabricated on a cellulose substrate by digitally printing graphite ink. The ink can be applied using automatic controls with high precision and accuracy. The graphite ink was diluted with a proprietary solvent (Ercon ET160) 55:45 w/w to obtain desired consistency for printing, and the mixture was homogenized using a tip sonicator to create a uniform dispersion. Using this printing technique, large numbers of sensors can be printed with high accuracy (FIG. 15B). (Other printing techniques such as screen printing or reel-to-reel printing can, of course, also be used for increased throughput). The individual electrode pairs can be cut out from the sheet and electrical contacts can be applied. An enlarged view of a single interdigitated electrode design is shown in FIG. 15C; the interdigitated design can provide increased area of the electrodes and greater signal-to-noise ratio. This design also allows rapid access of humidity to the paper. The sensor can be integrated into a variety of surfaces, such as a mask (shown in FIG. 14A) or into packaging where they can be used to detect or monitor packaging contents (see FIG. 16O).

As discussed in more detail below, changes in the ionic conductivity of the sensor can be detected by measuring the output current of the sensor when a bias, e.g., 25 V DC voltage, is applied between the electrodes of the sensor. However, other detections means are also contemplated, such as electrical resistance, or conductance, as these parameters are all linearly related by Ohms Law.

Figure 10A:
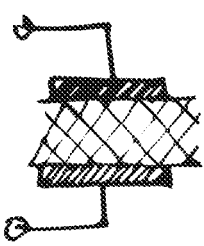
Figure 10B:
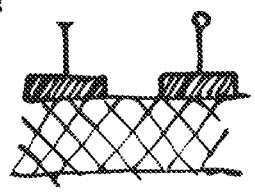
Figure 10C:
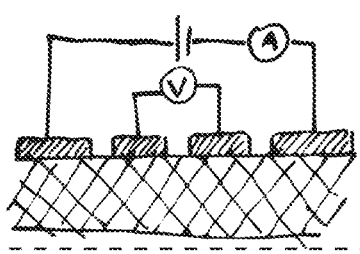
Figure 10D:
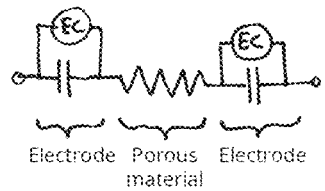
Figure 10E:
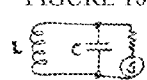
Figure 10F:
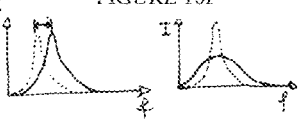

The sensor can be measured using any method in which currents are measured. For example, the sensors can include two electrodes (two point measurement). See, FIG. 10A. In a two point system, voltages is applied between two electrodes and current is measured through the electrodes. In other embodiments, the sensors can include four electrodes (four point measurements). See, FIG. 10B. In a four point system, voltage is applied between two electrodes and current is measured through these two electrodes and further voltage is measured on other two electrodes (four point measurement), as shown in FIG. 10C. FIG. 10D is an equivalent circuit for the sensor, in which EC stands for the electrochemical reaction with the gas to be sensed. In the case where the sensor is used to measure humidity, the electrochemical reaction can be the electrolysis of water. The applied voltage can be AC or DC, and the AC voltage can be applied over a range of frequencies. Exemplary voltages can be in the range of 5-50V. When current corresponding to multiple voltages is analysed, the analysis can include amplitude analysis and/or phase analysis depending on input signal frequency. In other embodiments, capacitance and resistance of the sensor can be calculated from the spectra or transient signal analysis. In one or more embodiments, the sensor is coupled with an LC resonator (an electric circuit consisting of an inductor, represented by the letter L, and a capacitor, represented by the letter C, connected together). FIG. 10E shows the resonance circuits and sensors used in the circuits. The sensor state changes resonance frequency or Q-factor of the LC resonator, as is shown in FIG. 10F. In one or more embodiments, the sensor is read wirelessly. The sensor can include an radio frequency ID (RFID) for this purpose.

In one or more embodiments, the response sensitivity can be increased by including additives in the paper device. In one or more embodiments, the ionic strength of the adsorbed water layer (and the corresponding ionic conductivity) can be increased by addition of salts to the layer. The salt can be soluble (highly soluble or moderately soluble) under the normal operating conditions of the sensor (humidity and temperature). Solubility of the salt can be modulated by the gas or vapor to be sensed. In one embodiment, the solubility of the salt is increased by the gas or vapor (salt dissolves). In one embodiment, the solubility of the salt is decreased by the gas or vapor (salt precipitates). As the salt dissolves (or precipitates), the ion concentration changes and, with it, the ionic conductivity of the porous material.

By way of example, water soluble salts such as sodium and potassium chloride, potassium nitride and potassium phosphate can be used. The salts can be applied by wetting or dipping the paper with a selected amount of salt solution. Exemplary loads for the device include dipping the substrate in a 10 mM aqueous NaCl solution and subsequently drying it at room temperature. The increased ion concentration improves the current output of the device which in turn increases the dynamic range of operation at lower relative humidity levels.

In other embodiments, the amplifier or amplification agent can be an organic molecule and the ionic conductivity of the organic molecule can be modified by the vapor or gas oxidizing, reducing or cleaving the organic molecule. In other embodiments the ionic conductivity changes by binding of the target molecule to the organic molecule or by polymerization of the organic molecule. In one or more embodiments, the gas or vapor are more charged or less charged than the original molecule, resulting in an increase or decrease in the measured conductivity, respectively. In other embodiments, the oxidized ore reduced form of the organic molecule changes the pH of the water absorbed on the surface of the porous substrate. In one or more embodiments, the organic molecule is bound to the target vapor gas and is less mobile (with a corresponding change in ionic conductivity). In one or more embodiments, the organic molecules binds to the surface of the porous substrate, thereby reducing its mobility. In one or more embodiments, the polymerized organic molecule turns into a gel and the gel layer changes the mobility of ions in the absorbed water. The additive can react with the gas or vapor reversibly, forming a real time sensor, or irreversibly, forming a memory sensor. The memory sensor does not require constant readout, but records, if it has been ever exposed to the gas or vapor. Non-limiting examples of amplification agents include $SO_2$ and $NO_2$, which can act as catalysts to polymerize vinyl compounds such as methacrylates. In aqueous environment NOx can be also be used as oxidizing agents. Suitable organic molecules have low volatility, and would not evaporate from the sensor over its lifetime. Ionic compounds, salts, large molecules such as proteins and large polar or charged molecules do not evaporate readily and are suitable organic molecules.

In one or more embodiments, an amplification agent can be included in the paper to amplify the signal generated by a target gas. Weak acidic or basic gases, for example, do not fully ionize in water and the device response can be amplified by increasing their dissociation into ions. In one or more embodiments, the signal of the sensor is amplified by adding an amplifying agent such as inorganic powders into the paper. The loaded powder reacts with the weak base (or acid) itself and dissociates in the aqueous electrolyte as ions and further increases the ionic conductance of the sensor. By selecting powders with different properties, the selectivity of the sensor can be tuned.

In one or more embodiments, where the sensed gas is ammonia, ZnO can be used as an agent for amplification. $NH_4OH$ (the hydrated form of ammonia gas), which does not dissociate completely in water, can dissolve ZnO and form ions such as $[Zn(NH_3)_4]^{2+}$ and OH—, shifting the equilibrium ion concentration and increasing the total number of charged species and the overall ionic conduction of the sensor. The ions revert back to ZnO in the absence of $NH_4OH$, thus ZnO acts as a reversible amplification agent.

In one or more embodiments, the additive can be a catalyst. The catalyst can be selected to facilitate a reaction that provides a stronger signal. For example, the catalyst can change the gas or vapor molecule into a charged molecule, change the acidity of the dissolved gas or molecule, or polymerize the gas or vapor molecule. In one or more embodiments, the catalyst can be a metal particle, alloy particle, organometallic complex, or biological enzyme. In one or more embodiment, the catalyst is an enzyme, such as carbonic anhydrase (that can be used to detect carbon dioxide). In one or more embodiments, the catalyst can be inorganic oxides, nitrides or sulfides.

In one or more embodiments, a suppression agent can be added to the paper to suppress signals from background gases that may interfere with the gas detection of interest. In one or more embodiments, a suppression agent can interact with interfering gases and reduce their ionization so that the presence of such gases does not interfere with target gas detection. By way of example, interference of other gasses can be prevented by addition of gas selective membranes, which would selectively allow diffusion of gas of interest into the paper substrate. With this method, the sensor can be engineered for the specific application.

As discussed in greater detail herein below, it may be desirable to monitor humidity (or water vapor) as the gas of interest. A humidity sensor can be useful, for example, as a respiration monitor. However, in certain embodiments, the ambient water vapor may interfere with monitoring and detection of other gases. In one or more embodiments, the contribution to the current signal derived from background water content can be accounted for. The amount of water adsorbed onto the cellulose fibers is affected by the relative humidity. See, e.g., FIG. 4. The greater the relative humidity, the greater the adsorbed moisture content of the paper. Higher moisture content generally corresponds to higher background conductivities, which can interfere with the measurement of target gas presence and concentrations. In one more embodiments, the sensor device adjusts for the relative humidity and accounts for the contribution to the measured conductivity due to it. In one or more embodiments, the relative humidity is determined independently and a correlation curve of conductivity to relative humidity is used to calibrate the device before, during or after operation and read out. In other embodiments, the device includes a reference detector that measures current for ambient in the absence of the target gas and adjusts the target gas reading accordingly.

The sensors can be used in various arrangements and combinations. In one or more embodiments, multiple sensors are incorporated into the device. The sensors can be the same or different. In one or more embodiments, multiple sensors capable of detecting the same gas or vapor are incorporated into the detection system. The multiple sensors can be used for spatial resolution of gas composition, e.g., humidity, differences. In other embodiments, the multiple sensors can be used for spatial resolution of differences in gas flow. In other embodiments, the sensors can have different additives. As a result, the sensors can have different sensitivity to different gases and vapors. This may be helpful to detect gas concentrations in situations where cross-sensitivity of gases occur. In other embodiments, one of the sensors can serve as a reference sensor. For example, one sensor can be a humidity sensor to detect background humidity and the second sensor can detect the gas of interest. In one or more embodiments, the output signal or signals of the senor system are calculated from the signals of two or more individual sensors. In one or more embodiments, the two or more sensors are connected to trainable or self-training machine learning systems. In one or more embodiments, the output signal of the sensor system correlates with the presence of a gas or vapor.

In one or more embodiments, the one or more sensors are mounted on a carrier substrate. The carrier substrate can be water impermeable, or elastic, or equipped with adhesive layer for mounting. The carrier substrate can contain holes for the flow of gas or vapor, or contain electronic circuitry for signal processing. The electronic circuitry can be flexible.

In one or more embodiments, the sensors are encapsulated in another material or in between layers of another material. The other material can be semipermeable to gas or vapor. In one or more embodiments, the other material can be a hydrophobic material and the material can be hydrophobic paper or porous fluoropolymer. The layer can be impermeable for water, but permeable for water vapor.

In one or more embodiments, the sensor system contains a structure to direct flow of gas or vapor. The structure can direct gas through the porous substrate or along the surface of the porous substrate.

In one or more embodiments, calibration information can be stored on the sensor. The information can be stored using a QR code, bar code, RFID (radio frequency ID), or electronic chip. In one or more embodiments, the calibration information is stored in a database and the sensor contains the ID to address the calibration information in the database. The ID can be stored using a QR code, bar code, RFID (radio frequency ID), or electronic chip.

In one or more embodiments, the sensor system includes an electronic circuit. The electronic circuit can be directly manufactured or mounted on top of the porous material of the sensor. In one embodiment, the electronic circuit is mounted on a separate substrate and interfaced with the porous material of the sensor. In one embodiment, the electronic circuit contains passive components (e.g., capacitance, resistance, or inductance). In one or more embodiments, the electronic circuit is used to read the sensor value. In one or more embodiments, the electronic circuit is an analog or digital circuit. In one or more embodiments, an external radio frequency is used to power the circuit. In one embodiment, the circuit contains a resonator/oscillator. In one embodiment, the sensor signal changes the resonance frequency of the oscillator or the Q factor (for damping) of the oscillator.

In one or more embodiments, the sensor includes active components (e.g., transistors or integrated circuits). In one or more embodiments, the circuit contains one or more energy storage or harvesting elements, such as a battery, a thermocouple, a solar cell or an inductive coil. In one or more embodiment, the sensor is used to collect and store the signal from the sensor, transmit the signal using radio frequency or transmit the signal using light or IR radiation.

In one or more embodiments, the sensor includes an external electronic circuit. And the electronic circuit can read the sensor and transmit the read data wirelessly. In one or more embodiments, the sensor is Internet enabled. In one or more embodiments, the receiving device further sends the data to a database, e.g., the cloud.

The following calculation provides a simple theoretical estimate for the change in current caused by exposure of the sensor to ammonia. The change in current is considered to correlate to the change in ionic conductivity of water absorbed on the surface of the paper. The estimated area of the electrodes, is calculated to be $A=17.5$ mm$^2$. The density of paper is measured experimentally to be $\rho=18.2$ mg/cm$^2$. The thickness of the paper is $h=350$ μm. The water content of the paper is $\eta=10\%$, at a relative humidity of 70%. The density of water is $\rho_w=1$ g/cm$^3$. The amount of water between the two electrodes is calculated by the following equation 1:

$$m_{water} = A\rho\eta \approx 3.2 \text{ mg} \qquad (1)$$

In one model, paper is viewed as a 3D cubic network of identical fibers. In this case, only vertical fibers would contribute to the conductivity, as horizontal ones lie in planes that are of equipotential. Only ⅓ of the water, therefore, contributes to the conductivity of the sensor. If we would condense all this water to single bulk volume, the effective surface area of water through the thickness of a single sheet of paper is given by equation 2:

$$A_{water} = \frac{A\rho\eta}{3h\rho_w} \approx 0.3 \text{ mm}^2 \qquad (2)$$

3600 ppm of ammonia yields a partial pressure of 360 Pa. According to dissolution equilibrium of ammonia, the concentration of ammonia in water is $\alpha=0.4$ wt %. NH$_4$OH has a pKa of 9.245, therefore, $\beta=2.5\cdot10^{-5}$, which is the ratio of the concentration of dissolved ammonia to the concentration of ammonium hydroxide (NH$_4$OH). The molar mass of ammonia is $M=17$ g/mol. The ionic concentration in water is therefore described by equation 3.

$$c_{ions} = \frac{\rho_w \alpha \beta}{M} \approx 5.8 \text{ μM} \qquad (3)$$

The specific conductivities of NH$_4$ and OH ions are $\lambda_{NH4}=7.34$ mS m$^2$/mol and $\lambda_{OH}=19.9$ mS m$^2$/mol, given a total value $\lambda=\lambda_{NH4}+\lambda_{OH}=27$ mS m$^2$/mol. All together we estimate the conductivity of the sensor using equation 4.

$$\Delta\sigma = \frac{c_{ions}\lambda A_{water}}{h} = \frac{\rho\alpha\beta\lambda A\eta}{3h^2 M} \approx 13 \text{ μS} \qquad (4)$$

In the case of an applied voltage of $U=25V$, we have $\Delta I=\Delta\Gamma U\approx3.3$ μA. This predicted change in current is ~10× higher than the measured change in current of ~300 nA. These two values are in good agreement considering the basic assumptions made above for the calculation of the predicted change in current.

The sensors can be used in a variety of applications. In one or more embodiments, the sensor can be used to monitor humidity in packaging.

In one or more embodiments, the sensor is sensitive to organic decay (amines are a common degradation product in meats and other protein containing products). The sensor can be included inside a food package, that can contain meats. The sensor can be sensitive to amines or ammonia and provide an indication of the freshness of the food product. The sensor can include an enzyme.

In one or more embodiments, the sensor is used to sense indoor living environment. The sensor can be integrated into a wall of a building.

In one or more embodiments, the sensor can be used to monitor a drying process, such as the drying of concrete, clay or wood.

In one or more embodiments, the sensor is used in agriculture, and the sensor is used to monitor moisture content in soil, in live or harvested crops or in hay.

The invention is exemplified in the following examples, which are presented for the purpose of illustration only and are not intended to be limiting of the invention.

EXAMPLE

Three gases, ammonia (NH$_3$), acetone and ethanol, were evaluated. NH$_3$ was obtained simply by collecting the vapor of a solution of aqueous ammonium hydroxide (NH$_4$OH). The partial pressure of NH$_3$ released from the solution of NH$_4$OH correlates directly with the concentration. For a 4% solution of NH$_4$OH in water, at room temperature, the partial pressure of NH$_3$ is approximately twice that of H$_2$O. We assumed equal partial pressures for H$_2$O and NH$_3$ for solutions of NH$_4$OH that were below 2%. Acetone and ethanol are water miscible organic solvents, which do not dissociate in water. Organic gases that were miscible in water reduced the ionic conductivity of the sensor in a concentration-dependant manner.

Figure 3:
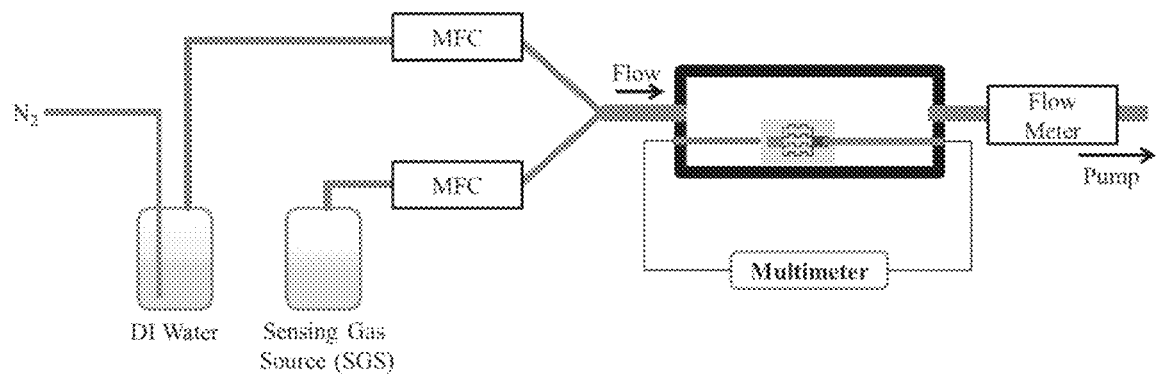
FIG. 3 is an experimental setup designed to deliver sensing gases to the test environment without a carrier gas to prevent parasitic effects.

To prevent the secondary drying effects of the carrier gases on the ionic conductivity of the sensor, a low pressure flow was used to pull the sensing gas from its source location. A schematic illustration of the test apparatus is shown in FIG. 3. Since N2 is bubbled through water to bring moisture into test environment more effectively, the carrier gas was eliminated only from the sensing gas delivery line.

The following tests for sensing NH$_3$ were conducted i) compared the response of the sensor at the same MFC flow rate before and after addition of NH$_4$OH to the water in the sensing gas source (SGS) bottle. Since water hydrates paper, it will naturally increase the ionic conductivity of the device and this experiment was designed to decouple the contributions NH$_3$ from only water, ii) compared the response of the sensor at different concentrations of NH$_3$, and iii) compared the response of the sensor with and without ZnO loaded in the paper.

The same experiments were conducted for both acetone and ethanol, with the exception of the effect of ZnO on gas detection, since ZnO does not dissolve in either of these solvents.

Paper sensors were prepared using a stencil, which was fabricated by removing features from a transparency (3M) using a laser cutter. Whatman chromatography paper (350 μm thick) was used for the substrate since its thickness prevents unintentional shorts between the printed electrodes on the front and the back-side of the sensor. Using the stencil, graphite ink (produced by Ercon) was brushed on the front and back of the paper to serve as the electrodes. The paper was cut into individual sensors and tested for electrical short-circuits using a multimeter (a resistance value of <20kΩ would indicate a short circuit) before use in any experiment.

Humidity Detection

Figure 4A:
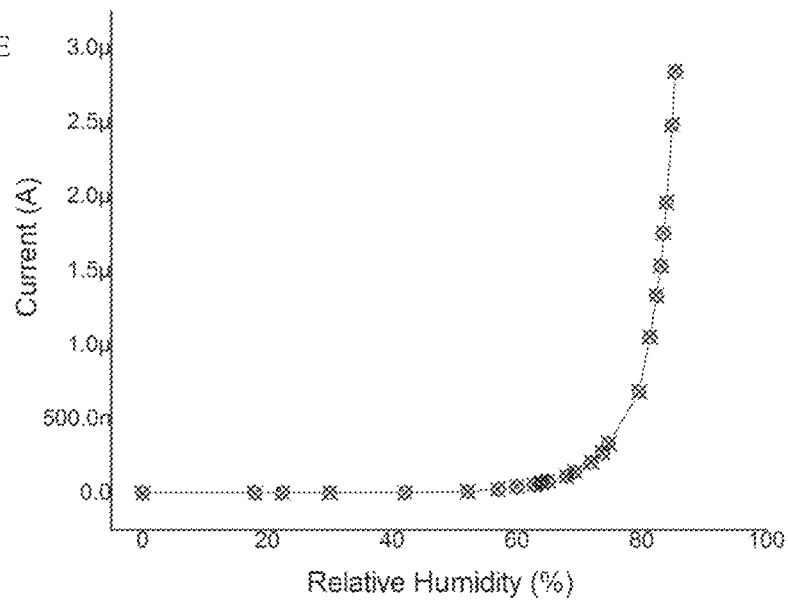
FIG. 4A is a plot of current vs. relative humidity (% RH) showing the measured output of the sensor with respect to relative humidity.

Since the sensor requires moisture to operate, its response to humidity was first determined. FIG. 4A is a plot of current vs. relative humidity and indicates the sensitivity of the device to changes in humidity. The sandwiched paper device, however, is able to detect changes in humidity from 40% up to over 85%, almost doubling the dynamic range of the sensor. The sensors, therefore, are intended to work in environments with humidity levels greater than 40% relative humidity.

Figure 4B:
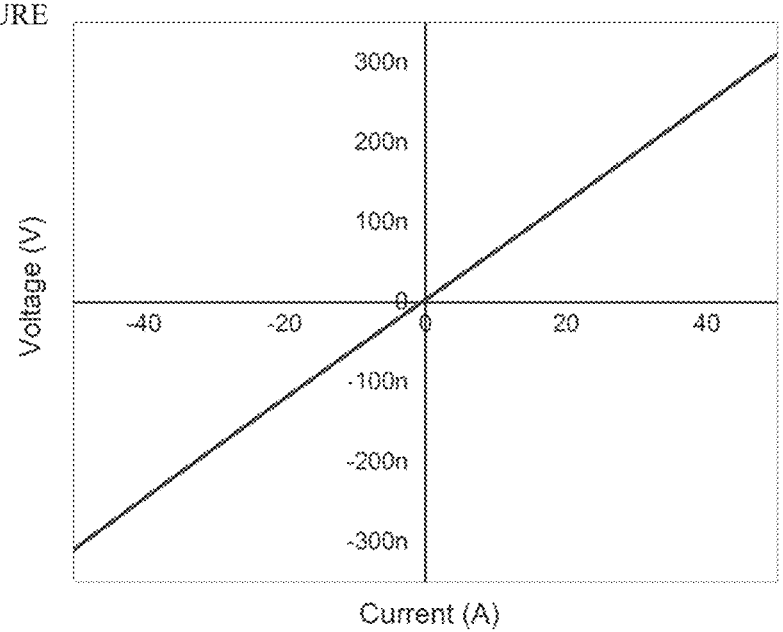
FIG. 4B is an I-V trace at 60% relative humidity.

The I-V characteristics of the device at 60% RH is shown in FIG. 4B. The plot was obtained by varying the source voltage between −50 V and 50 V and measuring the current passing through the sensor. The data indicate that the relationship is linear within the measured interval and the main limiting factor of the current in the sensor is the electrophoretic mobility of ions in the thin layer of adsorbed water on cellulose. For a typical electrochemical cell, where the current is limited by the Faradaic process, the current—voltage relationship would be nonlinear. In the current sensor device, however, the Faradaic process is not the dominant process and the output of the sensor below the potential for hydrolysis is beyond the accuracy of the instrumentation.

Ammonia Detection

For target gas detection, the device was operated at 25 V in all experiments. At a RH of 85%, the device requires only 75 μW.

The response of the sensor at different concentrations of $NH_3$ was measured by keeping the flow rate of water at a constant rate of 4000 sccm and varying the flow rate of $NH_3$ to the desired concentration. The percent concentration inside the measurement environment was calculated simply by dividing the flow rates of the gas and multiplying by 100%. A 1% mixture, therefore, would yield 10000 ppm. To test the response of the sensor in the presence of water only, a bottle containing 98 mL of distilled $H_2O$ was mixed with a hydrated stream of $N_2$ at a ratio of 80:4000 sccm. The response of the sensor is shown in FIG. 5A (top). Next 2 mL of 30% $NH_4OH$ was injected in the SGS through a septum which resulted in a 0.6% solution of $NH_4OH$ and 1200 sccm of $NH_3$ in the testing environment shown in FIG. 5B (middle). With the addition of NH4OH, the output of the sensor increased from 440 nA to 570 nA, indicating that the sensor is sensitive to $NH_3$. The graph in FIG. 5C (bottom) shows that timing of the pulses of gas (i.e., MFC State) with "on" indicating that the gas is flowing.

Figure 6:
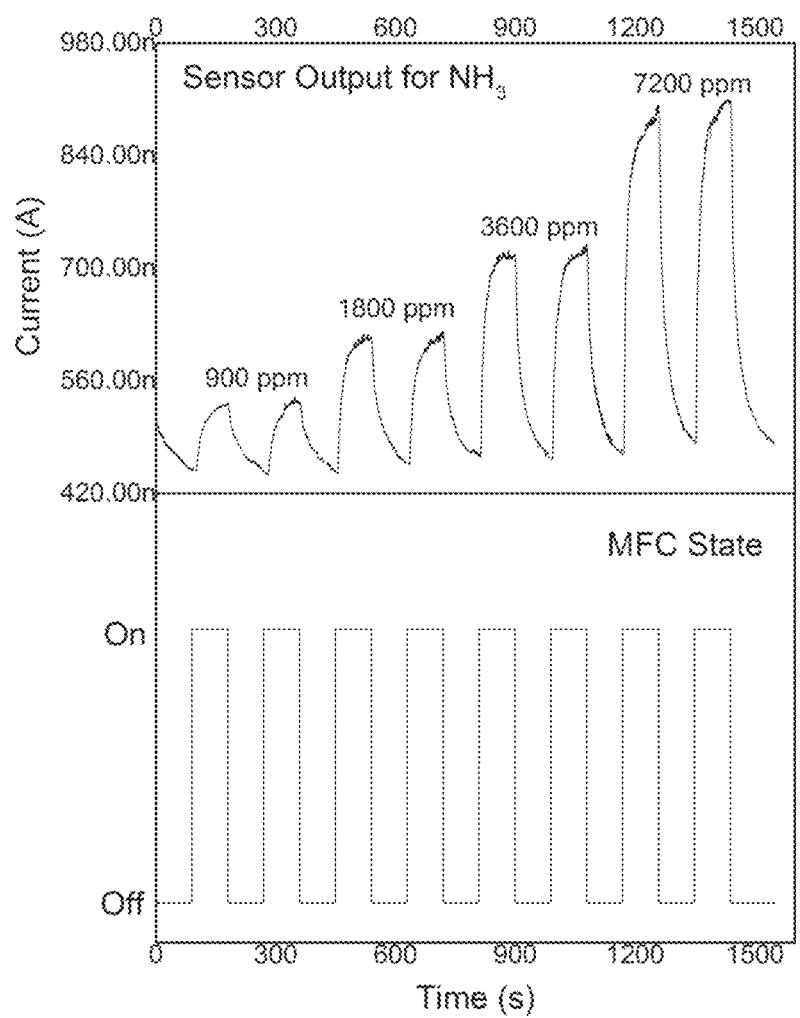
FIG. 6 is the plot of an output of the sensor at varying concentrations of $NH_3$ (top) along with pulse timing of the mass flow controller (MFC) (bottom).

FIG. 6 shows the response of the sensor at different concentrations of $NH_3$. These data show that the output of the sensor is dependent on concentration since the ionic conductivity of the moisture at the surface of the cellulose fibers increases. The higher concentrations of $NH_3$ produce more $NH^{4-}$ and OH-ions in the surface-bound water layer.

The changes in the ionic conductivity of the sensor when exposed to 3600 ppm of $NH_3$ at a relative humidity of 70% was approximated and the measured and calculated values of the ionic current were compared, assuming the adsorbed moisture in the paper substrate is bulk water. For an estimated sensing area of 17.5 $mm^2$ and a water content of 10%, the calculated change in current (ΔI), resulting from the ions generated by the dissociation of $NH_3$ in water, was 3.3 μA. Under the same conditions, the measured ΔI was 0.3 μA. Since water on the surface of the paper is not entirely acting like bulk water, and not all fibers are continuously and uniformly connected to each other, the calculated and measured values are in good agreement with each other. This result supports the model for the mechanism of how the sensor functions.

Acetone and Ethanol Detection

Figure 7:
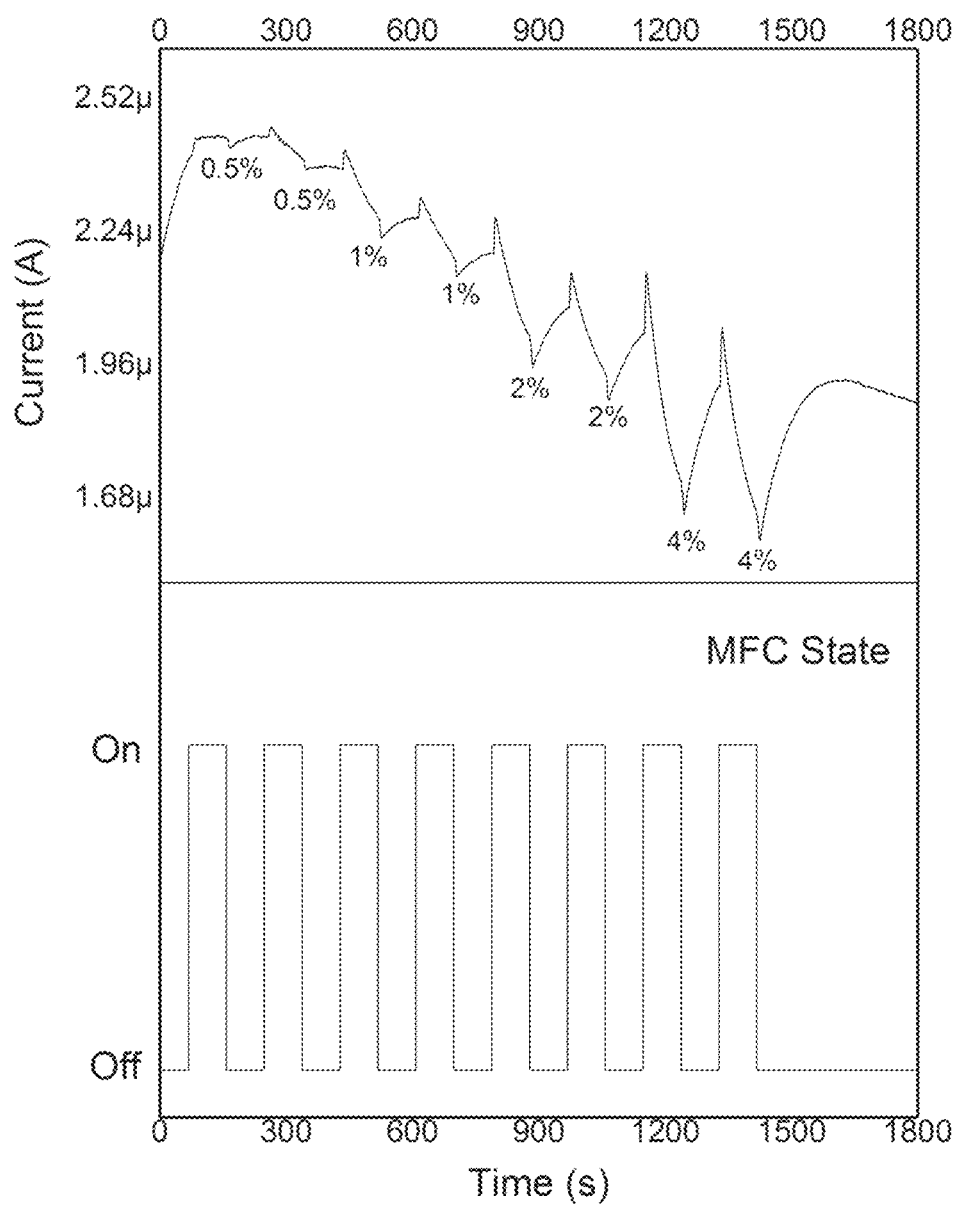
FIG. 7 is a plot of the measured output of the sensor when exposed to varying concentrations of acetone vapor along with pulse timing of the mass flow controller (MFC) (bottom).
Figure 8:
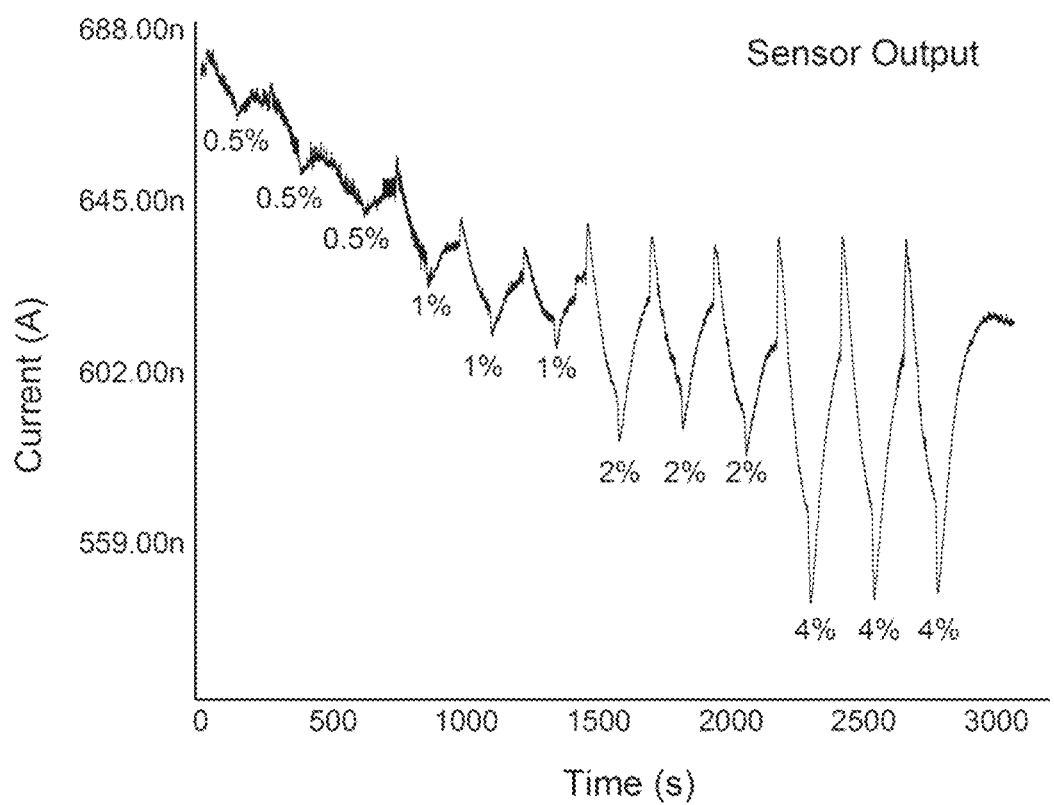
FIG. 8 is a plot of the measured output of the sensor when exposed to varying concentrations of ethanol vapor.

The response of untreated paper for gases of acetone (FIG. 7) and ethanol (FIG. 8) were also investigated. Both of these solvents are miscible in water, reduce the overall ionic conductivity of the sensor, and do not introduce new ions to the system. The sensor could measure both acetone and ethanol down to 0.5% (5000 ppm). The drift in the signal of the sensor is due to the slight change in relative humidity during the measurement. As discussed above, the effect of relative humidity can be accounted for, for example, by tracking the relative humidity using a commercially available detector and adjusting the readout accordingly to account for the humidity contribution to current readout.

Characterization of Paper Sensor Loaded with an Amplification Agent

The sensor was loaded with ZnO particles by dipping the sensor into a water based suspension of ZnO (25 mg ZnO powder in 50 ml of water) and letting it dry in an oven at 60° C. ZnO is known to be dissolved by $NH_4OH$, forming water soluble $[Zn(NH_3)_4]^{2+}$ ions.

Figure 9A:
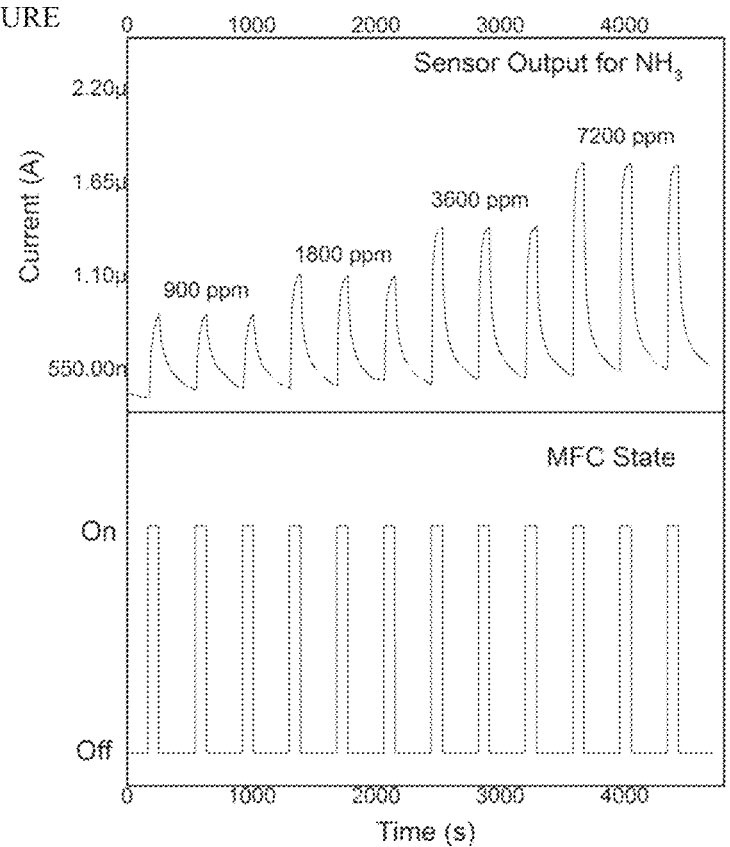
FIG. 9A is a plot showing an output of the sensor after loading ZnO powder on the substrate as an amplification agent along with pulse timing of the mass flow controller (MFC) (bottom)

In the presence of water, these ions dissociate to form ZnO when the supply of NH3 is stopped. By this mechanism, all of the $[Zn(NH_3)_4]^{2+}$ eventually returns to ZnO. FIG. 9 shows the response of the sensor at different concentrations of $NH_3$. The response of the sensor is reversible, repeatable, and dependent on concentration.

Figure 9B:
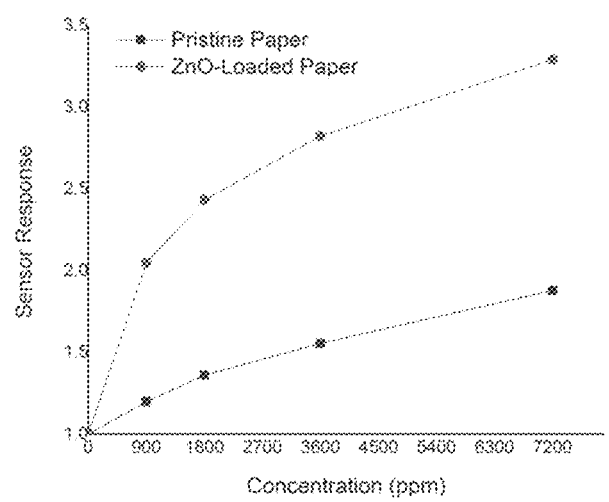
FIG. 9B is a plot showing sensor response for untreated and ZnO loaded $NH_3$ sensors, in which the sensor response was calculated by dividing the sensor output while $NH_3$ was continuously supplied ($I_{Gas-On}$) by the sensor output when the $NH_3$ supply was stopped ($I_{Gas-Off}$).

The response of the sensor was evaluated with and without the amplification agent and the results are shown in FIG. 9B. The signal from the sensor loaded with ZnO was more than double than the signal acquired from untreated paper, confirming that an amplification agent could improve the response and possibly sensitivity of the sensor. Other amplification agents can selectively measure other gases as well.

Porous Substrate-Based Respiration Monitor

A particular application of the sensors described herein is for the detection of humidity. This can be used to measure respiration in humans or animals. Systems and methods for measuring respiration are described with specificity in the description that follows; however, the various embodiments, system features and arrangement described above for the detection of vapors and gases apply equally here.

In one aspect of the invention, a porous substrate-based, e.g., a paper-based, moisture sensor is provided that uses the hygroscopic character of paper (i.e. the ability of paper to attract and hold water from the surrounding environment) to measure patterns and rate of respiration by converting the changes in humidity caused by inhalation and exhalation to electrical signals. The changing levels of humidity that occur in a cycle of inhalation and exhalation cause a corresponding change in the ionic conductivity of the sensor, which can be measured electrically. In one or more embodiments, the device can be equipped with electronics for wireless communications. By combining the porous substrate-based sensor with conventional electronics, data concerning respiration can be transmitted to a nearby smartphone or tablet computer for post-processing, and subsequently stored on a cloud server, or can be further analysed by a healthcare professional remotely. This means of sensing provides a practical solution to the problem of recording and analysing patterns of breathing. The sensors demonstrated a range of humidity sensitivity; however all show sensitivity at 65% RH and responsiveness is observed at less than 50% RH, less than 35% RH and as low as 20% RH.

In one or more embodiments, a respiration monitor is provided that monitors and provides information about the respiration rate of a user. Such information can be useful in monitoring breathing conditions such as involving apnea, hypopnea and respiratory arrhythmias, and other medical conditions.

In one embodiment respiration monitor is in communication with an actuator or feedback system, which operation is based on the input from the respiration monitor. Examples of such actuator or feedback could be breath stimulator or assistance, activation of inhalator to dispense a drug, alarm sound etc.

The sensor is capable of measuring the rate of respiration of a person by detecting the difference in moisture content of inhaled and exhaled air. The sensor can include a piece of paper (or other porous cellulose based substrate) with digitally printed graphite electrodes. In certain embodiments, the sensor can be embedded inside a flexible textile procedure mask (commonly used in hospitals). The sensor can be coupled to a low-cost, battery-powered standalone unit that can interface with an internet-enabled tablet computer/smartphone. The system can display and upload the collected data to the cloud, and thus enable healthcare professionals to remotely access the results. The paper sensor, electronics, and software transform a simple textile mask into a functional mask (with internet connectivity), which can measure, analyse, store, and share information concerning the rate and pattern of respiration of individual patients.

Device Design

For ease of reference, the respiratory sensor is described with referenced to paper as the substrate. However the principles described herein are readily applied to any porous hygroscopic substrate. Cellulose-based substrates such as certain textiles and fabrics, e.g., cotton fabrics, and paper are exemplary cellulose-based substrate. Cellulose paper has a very high affinity to ambient water. At a relative humidity of 70%, the moisture content in cellulose paper can be as high as 10% by weight. In addition to its ability to absorb high amounts of water from air, i) cellulose paper is inherently porous, a feature that allows gases to penetrate and interact easily with the bulk of the material in the sensor, ii) cellulose paper has a high surface area (over 100 $m^2/g$) so the sensitivity of the sensor is greater than thin films would have if operated using the same mechanism, iii) cellulose paper is chemically inert to most gases including highly corrosive species. The invention is demonstrated with a range of paper types, e.g., i) Whatman 1 Chr, ii) Whatman 3MM Chr and, iii) copy paper. Both Whatman 1 Chr and Whatman 3MM Chr papers are made of pure cotton cellulose fiber with a basis weight of 87 $g/m^2$ and 185 $g/m^2$. (The basis weight of paper is defined as the weight of paper per unit area). Other materials for use as substrates are within the scope of the invention.

When breathing out, the human breath is close to 100% RH, and therefore increases the amount of water on the sensor, thus, increasing its ionic conductivity. When breathing in, the amount of water on the surface of the cellulose fibers is reduced because the surrounding atmosphere almost always has a lower RH than exhaled air. This change in the amount of adsorbed water decreases the ionic conductivity of the sensor, as is illustrated in FIG. 14B. By applying a voltage between the two electrodes, the ionic conductance of the paper can be quantified based on the measured current. A change in the measured current provides an indication of change in relative humidity. This change is further used as an indication of exhalation (increase in RH) and inhalation (decrease in RH) of a patient. The paper sensor transduces variations in the level of moisture of its immediate surrounding to an electrical signal. Using this method, one can indirectly acquire accurately the respiratory signal of the patient. As the sensor itself measures changes in moisture content between the inspired and expired air, the system requires no calibration.

In one aspect, a paper-based sensor for detecting and monitoring respiration is provided. In one or more embodiments, the electrodes are disposed in close proximity on one side of the substrate. In some embodiments, the electrodes are interdigitated to increase the area of the area of the electrode, reduce the distance between electrodes and increase the signal to noise ratio. This design also allows rapid access of humidity to the paper. Contacts can be provided for connection to an external voltage source.

In other embodiments, the electrodes can be on the same side of the porous substrate, as is shown in FIG. 15A-15C. As shown in FIG. 15A, an electrode is fabricated on a cellulose substrate by digitally printing graphite ink. The ink can be applied using automatic controls with high precision and accuracy. The graphite ink was diluted with a proprietary solvent (Ercon ET160) 55:45 w/w to obtain desired consistency for printing, and the mixture was homogenized using a tip sonicator to create a uniform dispersion. Using this printing technique, large numbers of sensors can be printed with high accuracy (FIG. 15B). (Other printing techniques such as screen printing or reel-to-reel printing can, of course, also be used for increased throughput). The individual electrode pairs can be cut out from the sheet and electrical contacts can be applied. Contacts for connection to a voltage source can also be directly printed onto the substrate. An enlarged view of a single interdigitated electrode design is shown in FIG. 15C; the interdigitated design can provide increased area of the electrodes and greater signal-to-noise ratio. The high surface area and the small thickness of the paper improve the sensitivity of the sensor, since many ionically conductive paths connect the two electrodes and the electrodes are in close proximity, respectively. This design also allows rapid access of humidity to the paper.

Figure 2B:
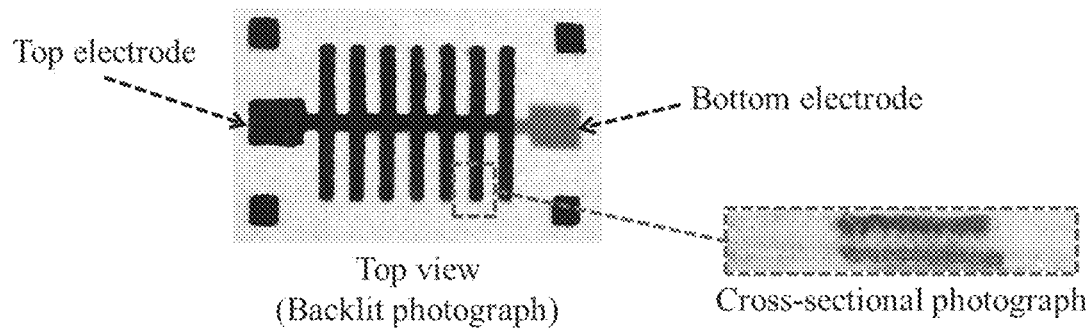

In one or more embodiments, electrodes are disposed on opposite sides of the paper detector, for example, by printing electrodes on both sides of a single sheet of paper. FIG. 2A is a schematic illustration of the fabrication of a device having electrodes on both sides using a stencil guide. Low-cost and easy-to-apply graphite ink is silk-screened onto a first side of the cellulose paper to form chemically inert carbon electrodes. Once dried and optionally heated, the paper is flipped and the counterelectrode is printed on the opposite side. Screen-printing allows fabrication of multiple devices on the same substrate; the electrodes can be designed to span a large surface area of the paper, to increase sensitivity of the device includes well-aligned electrodes on the front and back of the paper. FIG. 2B shows a backlit photograph of an actual sensor. A cross-sectional image visualizes the alignment of the top and bottom carbon electrodes.

The respiration monitor is mounted on a support that can be secured near, at or on the nose and/or mouth of the user. In one or more embodiments, the paper respiration monitor can be attached on the outer surface of a conventional doctor's mask, covering both the nose and the mouth. See, FIG. 16B. In this configuration, both nasal and oral breathing can be tracked. In other embodiments, the sensor can be secured, e.g., using an adhesive backing, in the vicinity, e.g., below, the nose. See, FIGS. 16A and 16D. The sensor system can include sensors individually positioned below each nostril. See FIG. 16C. The sensor can also be positioned to extend over the mouth. See, FIG. 16E. Sensor attachment can be accomplished in a variety of ways, such as over the nose bridge, or one or both ears, inside the nostrils, on a helmet, on a face or surgical mask, in a safety mask or emergency breathing masks and supplemental oxygen masks. See, FIGS. 16F-L. Because the sensor is small and light, it can also be adapted for use with infants. The sensor can be incorporated into infant head cover or attached to an infant bed. See, FIG. 16M-N. The sensor can be used during athletic training.

Figure 14A:
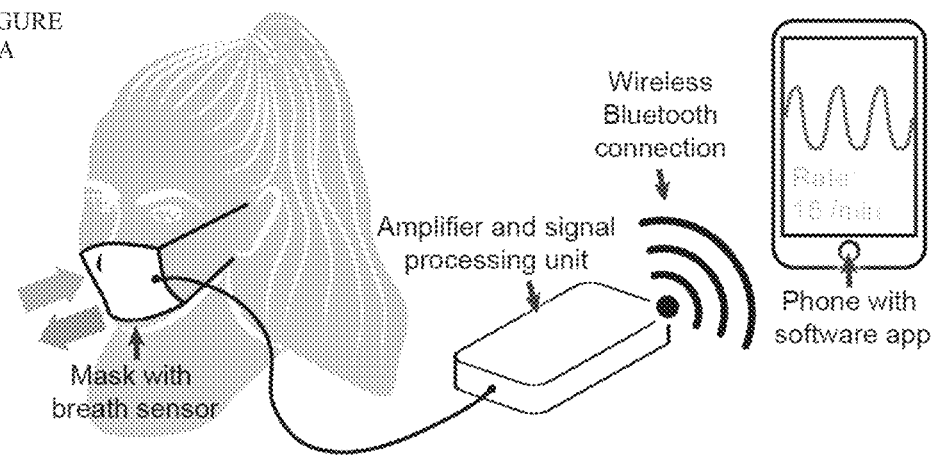
FIG. 14A is a schematic illustration of a facemask for respiration monitoring with the embedded paper-based sensor and electronics, including a wireless connection and phone with software app.
Figure 14B:
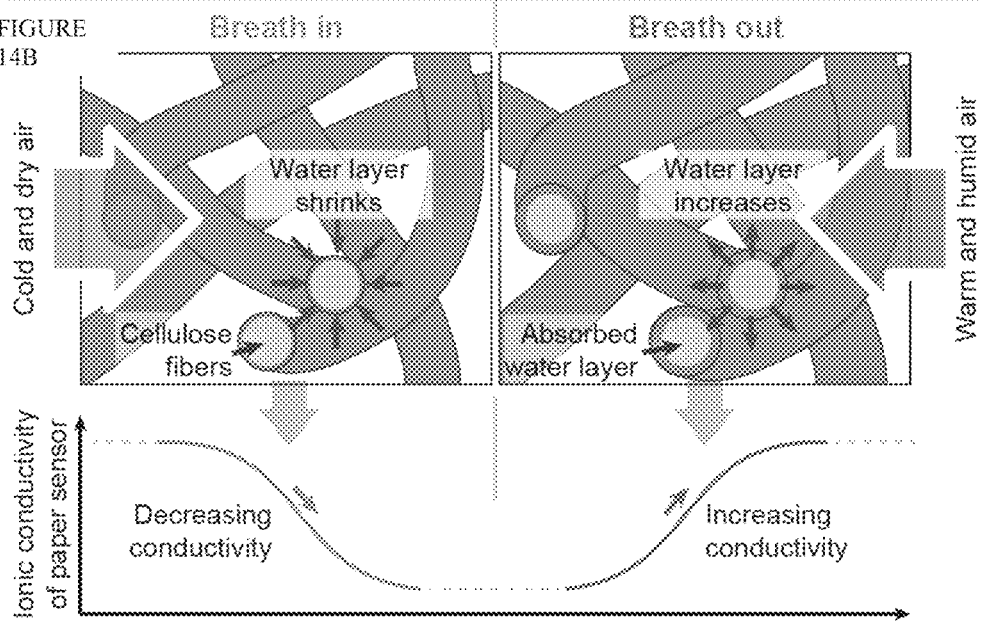
FIG. 14B is a schematic illustration of the mechanism of operation of a porous electrical respiration sensor according to one or more embodiments.

Low weight electronics and a power unit are mounted on the mask for wireless communication and signal read-out (see FIG. 14A). The collected data is transmitted to a nearby phone or computer, which can upload the data to the cloud. Changes in the water content of the sensor can be detected by applying a voltage, e.g., a 25 V DC voltage, between the carbon electrodes of the sensor and measuring the output current of the sensor. The power required for exemplary designs of the sensor is 175-250 µW at a RH of 90%. The power requirements can be substantially reduced through further optimization and redesign of the electrical circuit. In exemplary systems, the paper-sensor had the lowest power requirement among all of the electronic components used in construction of the system with a peak power consumption of 500 µW (<0.05% of the entire system). Thus, the power consumption is low and for instance, a single AA battery with a capacity of 2000 mAh at 1.5 V, can run an exemplary sensor continuously for 6000 hours or 250 days.

In other embodiments, other detections means are also contemplated, such as electrical resistance, voltage or conductance, as these parameters are all linearly related by Ohms Law.

In one or more embodiments, the sensitivity of the sensor and the output signal can be further improved by loading the sensor with a water-soluble salt than can increase the ionic conductance of the adsorbed water. For example, the paper of the paper-based sensor can be loaded with salts such as NaCl, KCl, $KNO_3$, or $HPO_4$. Loading of soluble salt can be accomplished in any conventional way, such as by dipping the sensor into a solution of soluble salt and drying the paper. Sensor sensitivity can also be modified by inclusion of other ions, such as inorganic compounds such as clays typically used in paper-making.

Humidity Detection

Han et. al. (J. Phys. Chem. C 2012, 116, 22094-22097) reported a paper-based RH sensor with copper tape electrodes applied to the surface of a sheet of paper with a separation distance of 2 mm. This design was only sensitive from RH 85% upward with very low conductivity (1 nS) resulting in lower current. For instance, at an applied bias of 25 V, their sensor would produce only 25 nA whereas the respiration sensor according to one or more embodiments of the current invention can produce over 10 µA response, an improvement of 400 fold. Thus, the design failed to achieve high sensitivity.

Three different kinds of papers were demonstrated in the paper sensors: i) Whatman 1 Chr, ii) Whatman 3MM Chr and, iii) copy paper. Both Whatman 1 Chr and Whatman 3MM Chr papers are made of pure cotton cellulose fiber with a basis weight of 87 $g/m^2$ and 185 $g/m^2$. The standard copy paper had a basis weight of 80 $g/m^2$.

Figure 11A:
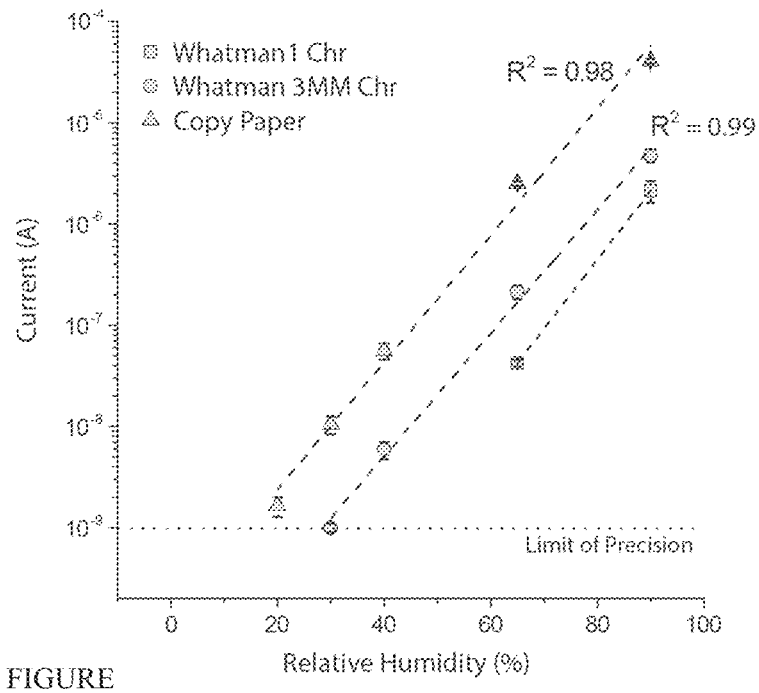
FIG. 11A is a plot of current (A) vs. relative humidity (% RH) showing the response of the sensor made with Whatmas1 Chr, Whatman 3MM Chr, and copy paper between 0-90% relative humidity with a 25V bias voltage across the two electrodes of the sensor.

The response of the respiration monitor to RH levels ranging from 0-90% (under an applied bias of 25 V) is determined. FIG. 11A is a plot of log current vs. relative humidity. The plot shows that the respiration monitor is sensitive above a RH of 20%. The copy paper showed the highest sensitivity. The difference in sensitivity between sensors fabricated with Whatman 3MM Chr and Whatman 1 Chr may be due to their basis weight. A larger area of cellulose fibers in a given area of paper would create a greater number of electrically conductive pathways at a given level of RH, reduce the overall resistivity, and increase the sensitivity. The high sensitivity of copy paper may be related to various sizing components, particularly clay, added in the papermaking process. Clay is added to create a smooth surface for increased printability. Added clay would increase both the concentration of ions in the paper substrate and the hydrophilicity of the system, and thus increase conductivity.

Figure 11B:
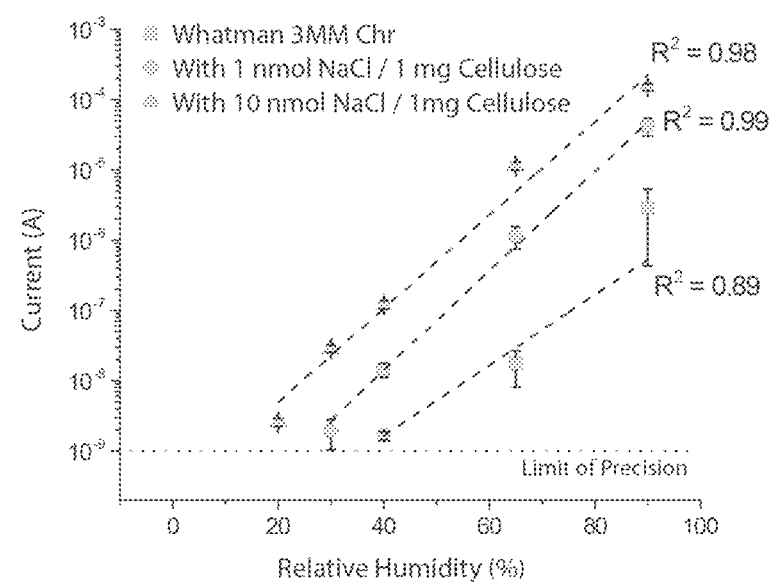
FIG. 11B is a plot of current (A) vs. relative humidity (% RH) showing the response of the sensor made with the same paper types when loaded with NaCl.

The electrical conductivity of pure cellulose paper can also be increased by the intentional addition of ionic species. FIG. 11B is a plot of log current vs. relative humidity for having 1 nmol NaCl/mg cellulose and 10 nmol NaCl/mg cellulose. The electrical conductivity of paper increased with the increasing salt concentration. Different NaCl salt loads can be introduced into the paper sensor by adding a salt solution to the paper and drying (prior to sensor fabrication). Loading of NaCl was done by dipping the sensor into a 10 mM aqueous solution of NaCl and drying the paper in an oven at 60° C. Using 1 mM and 10 mM solutions of NaCl, the addition of 100 nmol of NaCl resulted in a concentration of 1 nmol NaCl per 1 mg of cellulose and the addition of 1 µmol of NaCl resulted in a concentration of 10 nmol NaCl per 1 mg of cellulose. The response from the NaCl loaded sensor under an applied potential difference of 25V demonstrated an improved sensitivity. The use of NaCl in the sensor increased the ionic conductivity of the adsorbed water by an order of magnitude. Incorporation of salt provides a very simple route to fine-tune the electrical characteristics, and to improve signal-to-noise ratio and RH sensitivity of the paper-based moisture sensor.

The sensor operates a two-electrode electrochemical cell where water and other chemical species (e.g. dissolved salts) are electrolyzed in the presence of an applied potential across the electrodes. The oxidation and reduction of chemical species on the surface of the graphite electrodes produce an electrical current, measured using electronics. This current is proportional to the concentration of ionic species in the solution. The half-cell reactions for $H_2O$ and a dissolved salt in water (i.e. NaCl) are shown below in equation; as a result of the electrochemical process, formation of $H_2$ gas on the cathode and $Cl_2$ or $O_2$ gas on the anode is expected, depending on the NaCl concentration.

Figure 17:
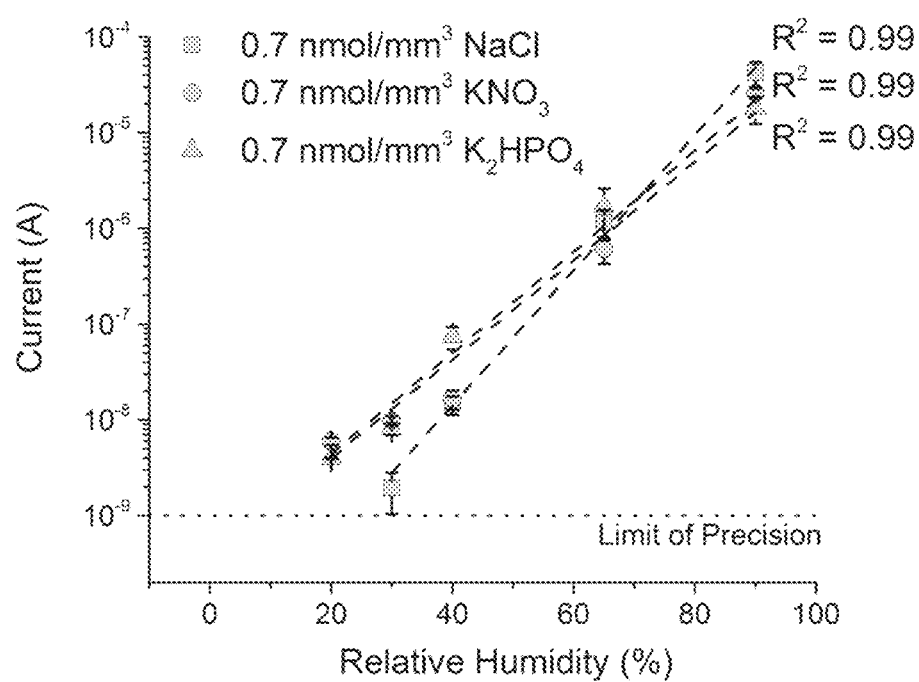
FIG. 17 is a plot of current (A) vs. relative humidity (% RH) showing the response of a paper sensor when loaded with NaCl, $KNO_3$, $HPO_4$.

Other materials could potentially be used to further improve the sensitivity of the sensor. NaCl can be replaced by other salts, such as $KNO_3$ and $K_2HPO_4$, which display a behavior very similar to that observed for NaCl (FIG. 17); This result confirms that various salts can be used to fine-tune the sensitivity and electrical characteristics of the paper sensor.

A weak dependence of the output current of the paper sensor on the temperature was observed (between 22° C. and 40° C.). This small difference may be due to an increase in the mobility of ions at elevated temperatures, and thus an increase in conductivity. The observed difference, however, was negligent and does not interfere with operation of the device.

In one or more embodiments, the paper sensor is not sensitive to $CO_2$. When a paper-based sensor is exposed to $CO_2$ concentration of 25% (at 70% RH), there was no increase in sensor output. This insensitivity may be explained by the low solubility of $CO_2$ in water (<0.5 g/liter at room temperature at 1 atm). The paper sensor is, therefore, largely sensitive to changes in the amount of moisture present in paper, and is not affected by the concentration of $CO_2$ in human breath (<5%).

Simulated Respiration Monitoring

Figure 12:
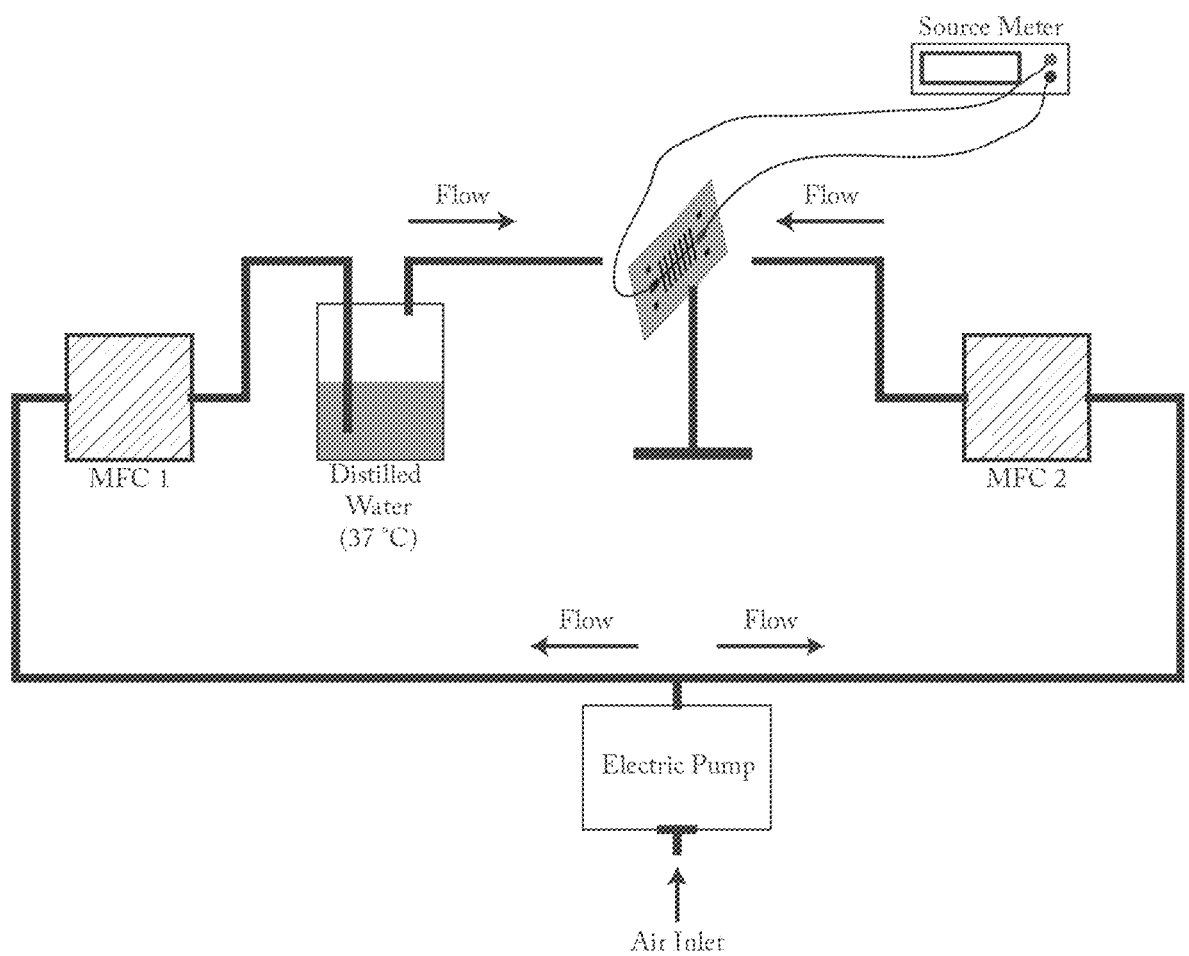
FIG. 12 is a schematic view of the constructed respiratory simulator for sensor evaluation, where two mass flow controllers (MFC) are configured to apply either humidified air (through water tank) or dry/ambient air and sensor electrical characteristics are measured with computerized source meter.

In order to simulate breathing of a human, a system was designed to flow air at precise rates over the sensor from a source of air at ~100% RH humidity and from atmosphere at ~70% RH. The 100% RH air mimics flow exhaled from the lungs and the 70% RH air mimics flow inhaled from the atmosphere. This system allows one to control precisely the frequency and flow rates of the air passing over the sensor; such control allows one to determine the response of the sensor to different conditions of respiratory arrhythmia. A respiratory simulator using two 1000 sccm mass flow controllers (MFC), manufactured by MKS, a Keithley source meter, and an electric pump to create airflow during testing of the sensor is shown in FIG. 12. All instruments were controlled using LabView programming software.

The simulated human breath (i.e., 100% RH) was created by bubbling ambient air through a container filled with distilled water, which was maintained at 37° C. The flow of humidified air was controlled by MFC 1, and the flow of ambient air was controlled by MFC 2, as shown in FIG. 12. During all of the simulation measurements, the RH of the ambient environment was measured to be ~70%.

Three sets of tests were performed, each consisting of 10 full cycles of flowing air of 100% humidity (i.e., breathing out) and 70% humidity (i.e., breathing in).

A healthy adult breathes between 6 to 12 breaths per minute, displacing up to 24 L of air per minute. For the testing setup, a lower airflow (max. 1 L/min) was used in order to demonstrate the sensor was sensitive to flow rates within the pathological region, which approached zero (i.e., apnea).

Figure 13:
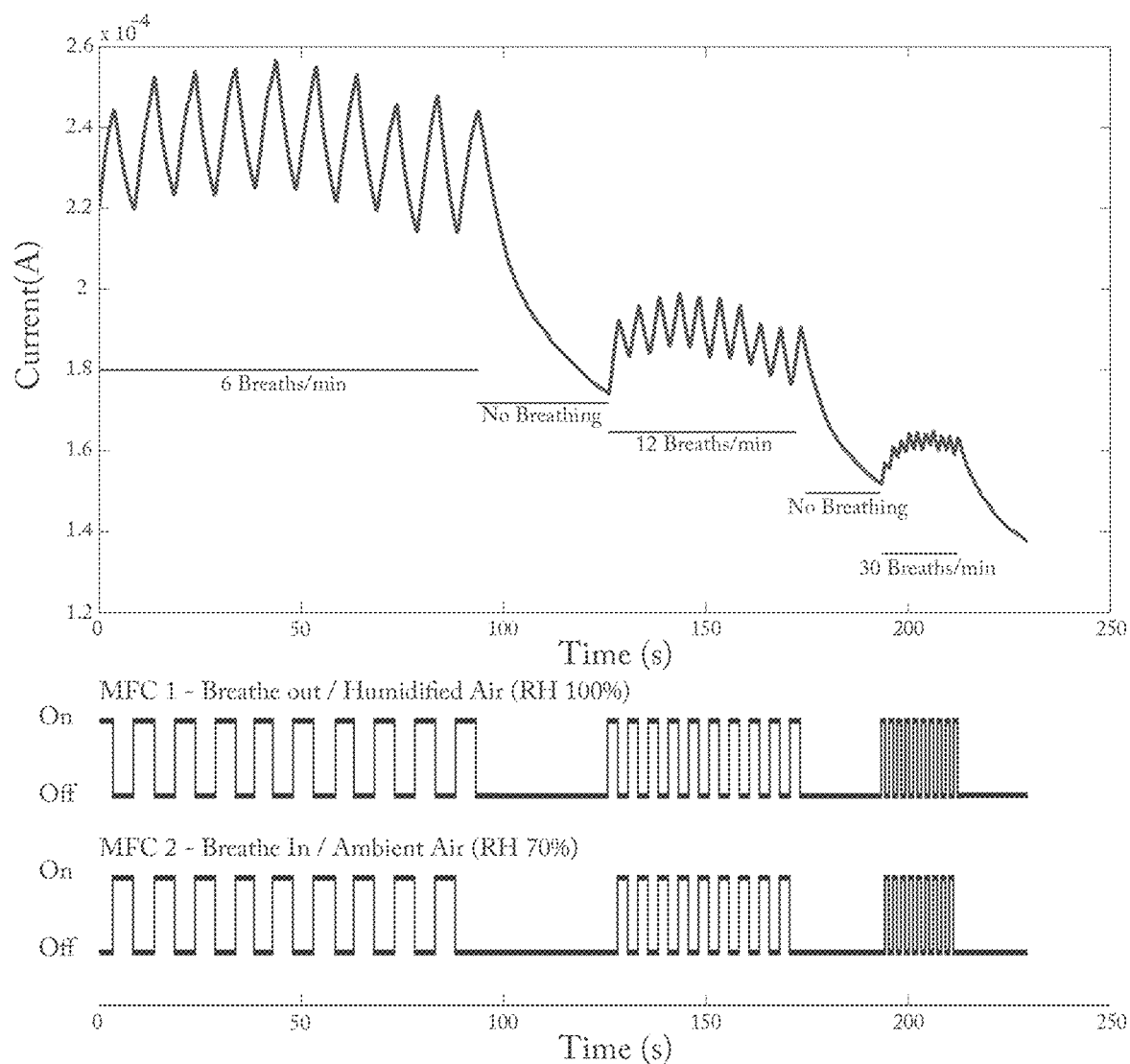
FIG. 13 is a plot of simulated breathing patterns and the response from a paper-based humidity sensor (loaded with NaCl) when exposed to a simulated breathing pattern, in which breathing was controlled by two mass flow controllers (MFC) of air with 100% humidity and air with 70% humidity (shown in lower section of figure) and the sensor had a 25V bias voltage across its two electrodes.

In the first test, the breathing rate was set to the lower end of the healthy breathing rhythm at six breaths per minute, breathing in and out every 10 seconds. The periodic airflow was halted through both MFC 1 and MCF 2 to simulate paused breathing (i.e. apnea). During this period of no flow, the output of the sensor decreased significantly, providing a detectable signal for diagnosis of apnea, as shown in FIG. 13.

After this period of no flow, regular breathing was continued and the breathing rate was set at 12 breaths per minute (with a flow rate of 0.8 L/min) followed by another period no flow. The simulator was then set to 30 breaths/min (with a flow rate of 0.5 L/min) to demonstrate the rapid response time of this sensor. See, FIG. 13.

Fast breathing with shallow breaths is a symptom of hypopnea and our sensor performed extremely well in all of the simulated scenarios of paused and shallow breathing, suggesting this sensor is suitable for diagnosing arrhythmias in respiration.

Recording and Analysis of Respiratory Signals

We placed our paper-based moisture sensors into low-cost textile procedure masks to demonstrate its use with healthy adults (FIG. 18A). We tested the functional mask on human volunteers.

We designed and fabricated a low-cost data acquisition device using off-the-shelf electronic components (FIGS. 18B and 18D). The reader electronics were purchased from Digikey (including the Arduino microcontroller). The printed circuit board (PCB) was designed using Eagle application package and was manufactured by Silver Circuits Sdb. Bhd., Selangot Malaysia. The Bluetooth shield, Kedsum KDF001A, for the Arduino board was purchased separately from Amazon. The housing for the electronics was designed using AutoCAD and printed with a Dimension 3D; Stratasys, Inc 3D printer in acrylonitrile-butadiene-styrene (ABS) thermoplastic polymer. The Android app was designed and implemented in the Android Studio development environment using Java and XML programming languages. We used a Samsung Galaxy Tab 4 tablet computer as the testing device.

This instrument generated a 25V DC potential from a 5V DC power source, and applied the voltage across the paper sensor. The unit amplified and digitized the resulting electrical current and transmitted the data to a tablet computer (FIG. 18C) over a wireless Bluetooth communication link. The custom-built Android application, with a minimally complex design, can display the incoming data and run simple analytics (e.g. Fourier transformations). The software can also save the collected results to a text file, which can be uploaded to the cloud, or emailed to a third party for off-site analysis. This feature will be particularly useful for individuals who monitor their respiration at home and wish to share their results remotely with a healthcare professional.

The Android application also has the option to apply finite-impulse-response (FIR) and infinite-impulse-response (IIR) digital filtering algorithms to the acquired signal. Digital filters are commonly used for the separation of combined signals and the restoration of distorted (i.e. noisy) signals. Since the system we implemented can also be used as a research tool, the user has the flexibility to design custom digital filters (e.g. low-pass, high-pass, band-pass, band-stop) to extract other metrics from the recorded pattern of respiration. The filter coefficients can be stored as a text file on the tablet computer and imported when the application is launched. Both the filtered and the raw data are recorded as a text file for later analysis. By implementing additional compressed sensing/sparse sampling algorithms, the size of the files containing the collected data can be made significantly smaller, allowing rapid transfer of these files at lower network speeds. This capability would be particularly useful in the developing world.

Figure 19A:
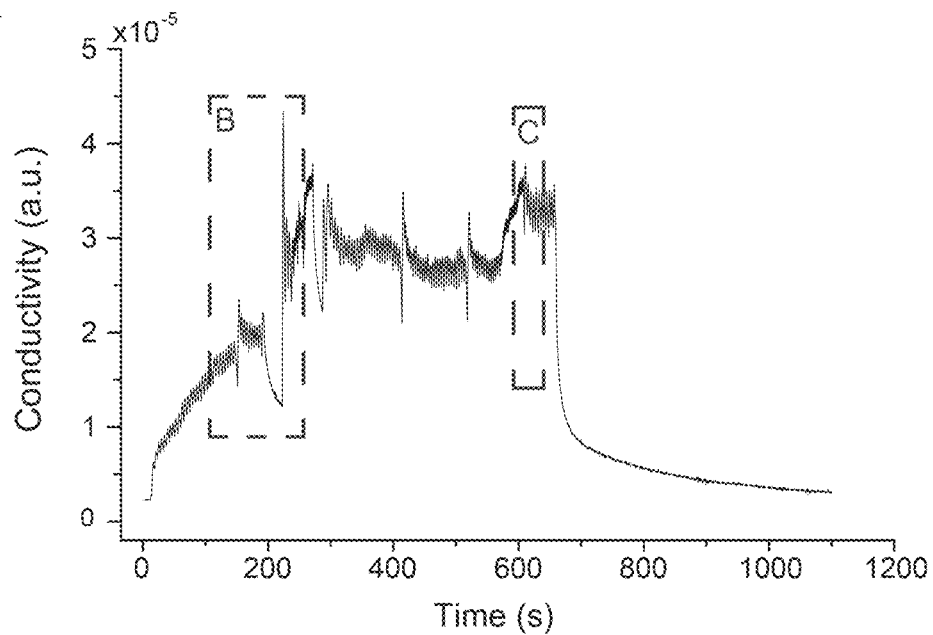
FIG. 19A is a plot of conductivity (a.u.) vs. time (s) showing the resting respiratory activity of a subject recorded using the functional facemask, in which the subject was asked to breathe normally, take deep breaths, pause and breathe randomly during the experiment.
Figure 19B:
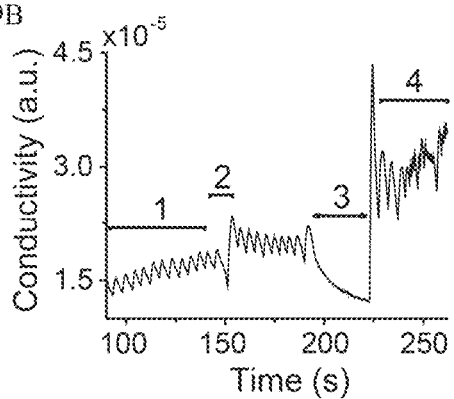
FIG. 19B is a plot of conductivity (a.u.) vs. time (s) showing breathing patterns recorded while: 1. breathing normally, 2. taking a deep breath, 3. paused and, 4. random breathing.
Figure 19C:
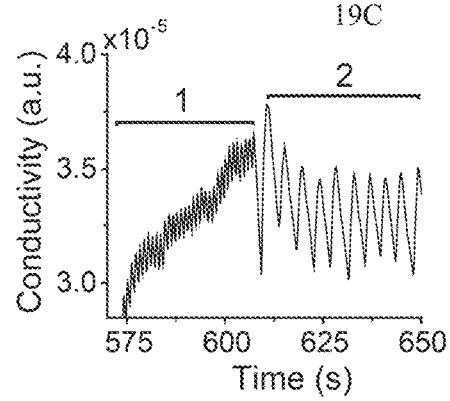
FIG. 19C is a plot showing the seamless transition between fast and shallow breathing (1) and normal breathing (2).

The functional textile mask was able to successfully track the respiratory activity of the subjects for 15 minutes at room temperature (FIG. 19A) while at rest (i.e. sitting in a chair); the duration of the experiment was limited due to the specifications of the IRB. There is a significant initial drift in the output of the paper sensor. The drift is caused by the large difference in drying and humidifying cycles during breathing, and reaches equilibrium in a few minutes. FIG. 19B displays a collection of different breathing patterns acquired during the experiment. The area marked with (1) is a normal breathing pattern (which consists of periodic breathing cycles of similar magnitude) followed by a deep breath marked as (2). During this period, the subject had a rate of respiration of 14 breaths per minute. A pause in breathing was registered as a drop in the recorded output current (3). A mixture of deep, slow, fast, shallow breathing patterns could also be accurately monitored during the experiment and marked as (4) in FIG. 5b. The device responded seamlessly to the transition between periods of fast, shallow and normal breathing (FIG. 19C). The system was also able to acquire and transmit all of the collected data to the tablet computer.

Figure 20A:
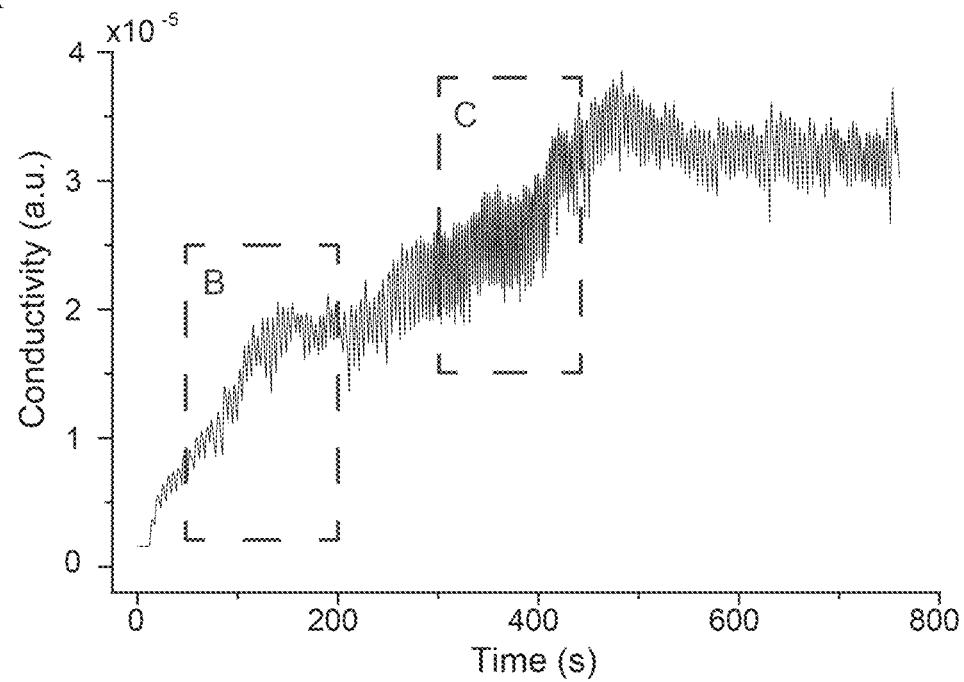
FIG. 20A is a plot of conductivity (a.u.) vs. time (s) showing recorded respiratory signal during light (FIG. 20B) and vigorous (FIG. 20C) exercise, in which the subject had an increase in the rate of respiration from 12 breaths/min during light exercise to 22 breaths/min during vigorous exercise.
Figure 20B:
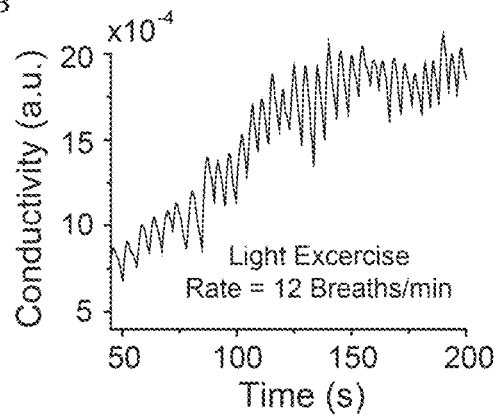
Figure 20C:
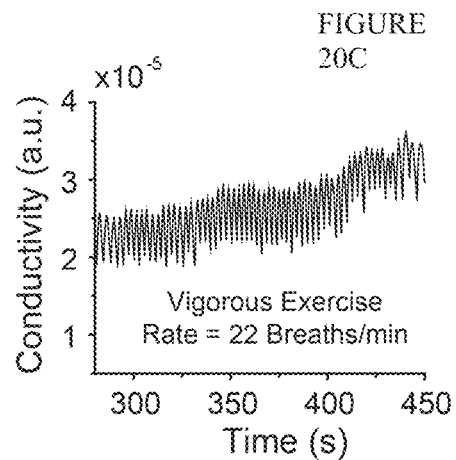
Figure 21A:
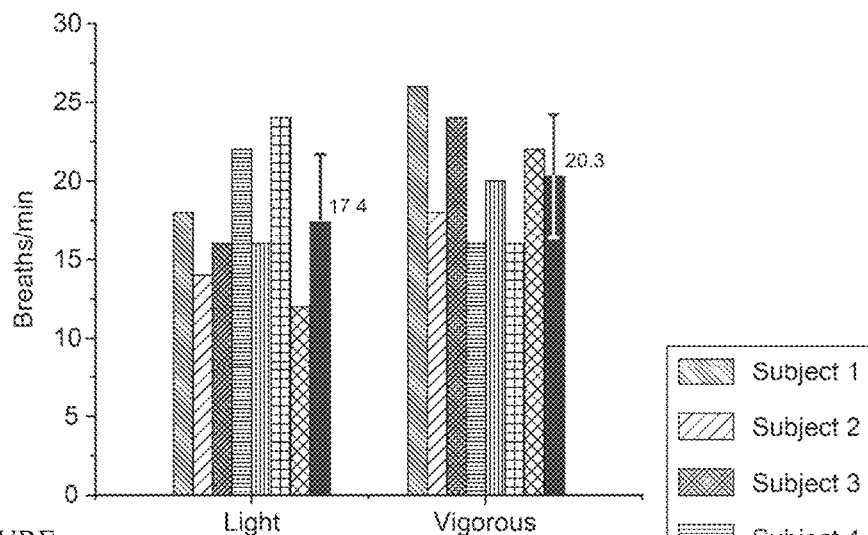
FIG. 21A is a bar graph of breaths/min for volunteers during light exercises (left) and vigorous exercises (right)

FIG. 20A-C shows a trial in which a subject took a short walk inside the building to test two performance factors of the system: I) noise levels in the collected data during movement, and II) system performance during light exercise (i.e. walking around the hallways) and vigorous exercise (i.e. high tempo climbing of four flights of stairs in the building). The signal-to-noise ratio for the collected data was very good during both light exercise (FIG. 20B) and vigorous exercise (FIG. 20C); the rate of respiration could easily be detected by counting the number of peaks. The subject registered a rate of respiration of 12 breaths/min during light exercise, and 22 breaths/min during more vigorous exercise. (The breath counts were calculated manually from the collected data). Interestingly, some of the subjects exhibited a decreasing rate of respiration when transitioning from light exercise (24 breaths/min) to vigorous exercise (16 breaths/min). The subjects compensated for this decrease by taking deeper breaths and the rate of respiration alone is not a sufficiently descriptive metric for the analysis of respiratory activity without data on the respired volume of the subject. FIG. 21A summarizes the rate of respiration of each subject during light and vigorous exercise.

Figure 21B:
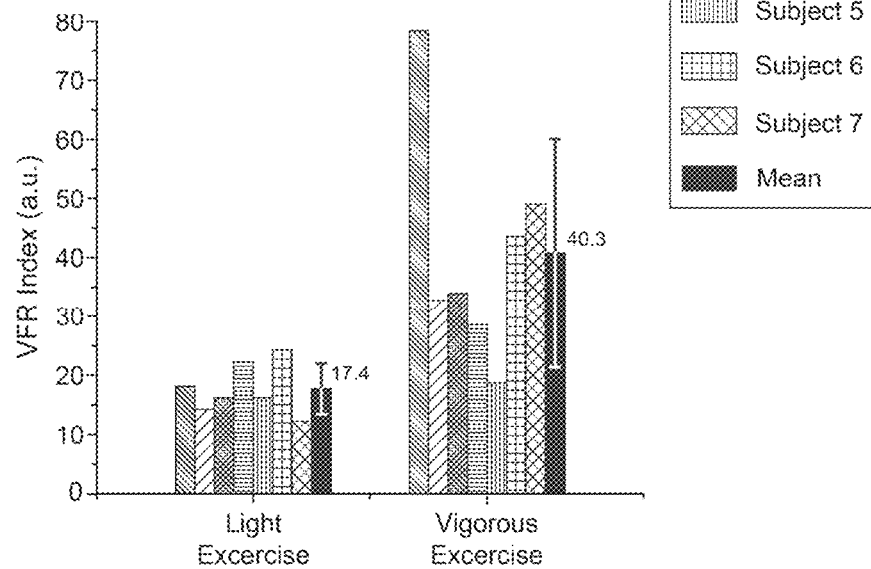
FIG. 21B is a bar graph of VFR (a.u.) for volunteers during light exercises (left) and vigorous exercises (right).

One of the biggest advantages of our device is its ability to capture the pattern of respiration, which contains information regarding the depth of breathing (exchanged volume) in addition to the rate of breathing. We have defined a new metric, the Volumetric Flow Rate Index (VFR Index), which is the product of the rate of respiration (RR) and the average signal amplitude normalized to a reference signal amplitude (FIG. 21B). Essentially, the amplitude of the captured cyclic signal is proportional to the volume of the inspired and expired air during respiration. This results in information about the depth of breathing (i.e. tidal volume). The formulas needed to calculate the VFR Index are shown below in equation (5) for light exercise and (6) for vigorous exercise.

$$VFR\ Index_{Light} = RR_{Light} \times \left(\frac{A_{Light}}{A_{Light}}\right) \quad (5)$$

$$VFR\ Index_{Heavy} = RR_{Vigorous} \times \left(\frac{A_{Vigorous}}{A_{Light}}\right) \quad (6)$$

Here, $A_{vigorous}$ is the average amplitude of the signal during vigorous and, $A_{Light}$, the light exercise. Using this approach, we determined that all of the subjects exchanged a larger volume of air during vigorous exercise than they did during light exercise, a conclusion that cannot be derived solely from the rate of respiration.

Overall, the paper sensor, electronics and the mobile app, performed without failure or interruption of data during the experiments, and thus have the potential to be used for monitoring breathing at rest and during physical activity. An inexperienced individual could learn how to read and interpret these graphs within a few minutes. Filtering out the drifting baseline using digital filters would further simplify the process of manual interpretation.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances. Percentages or concentrations expressed herein can represent either by weight or by volume.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments. Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise.

It will be appreciated that while a particular sequence of steps has been shown and described for purposes of explanation, the sequence may be varied in certain respects, or the steps may be combined, while still obtaining the desired configuration. Additionally, modifications to the disclosed embodiment and the invention as claimed are possible and within the scope of this disclosed invention. In particular, it is contemplated that features and embodiments that are described individually may be combined without departure from the invention.

What is claimed is:

1. A method of detecting respiration of a patient comprising:

providing a sensor comprising an electrode pair in electrical contact with a layer of hygroscopic porous cellulose paper material capable of adsorbing and desorbing water as a function of relative humidity;

positioning the sensor in the proximity of a mouth and/or nose of the patient; and monitoring the change in water content of the sensor over time by application of a voltage across the electrode pair, such that a current is induced that is proportional to the ionic content of water in the hygroscopic porous cellulose material, and wherein the increase and decrease in water content is correlated to exhalation and inhalation, respectively.

2. The method of claim 1, wherein the method detects a respiratory condition such as apnea, hypopnea and respiratory arrhythmia.

3. The method of claim 2, wherein the respiratory condition is one or more of apnea, hypopnea and respiratory arrhythmia.

4. The method of claim 1, wherein the response is an increase in current, indicating an increase in the adsorbed water in the sensor.

5. The method of claim 1, wherein the response comprises one or more of current, electrical resistance, voltage, or conductance.

6. The method of claim 1, wherein said response is wirelessly transmitted from the sensor to a remote location.

7. The method of claim 1 wherein a microcontroller is used to process the response of the sensor to generate data representative of said change of water content over time in an exhaled gas stream.

8. The method of claim 1, wherein the increase and decrease in water content is used to generate data representative of breathing rate.

9. The method of claim 1, wherein the increase and decrease in water content is used to generate data representative of breathing depth.

10. A respiration monitor, comprising:
a support capable of being positioned in the proximity of a mouth and/or nose of a patient; and
a sensor comprising an electrode pair in electrical contact with a layer of hygroscopic porous cellulose paper material capable of adsorbing and desorbing water as a function of relative humidity, said sensor attached to the support and located so as to be in the proximity of patient inhalation and exhalation, wherein upon application of a voltage across the electrode pair, current is induced that is proportional to the ionic content of water in the hygroscopic porous cellulose paper material.

11. The respiration monitor of claim 10, further comprising an amplification agent in or on the hygroscopic porous cellulose paper material.

12. The respiration monitor of claim 10, further comprising a damping agent in or on the hygroscopic porous cellulose paper material.

13. The respiration monitor of claim 10, wherein the hygroscopic porous cellulose paper material comprises woven textiles, non-woven textiles, non-woven meshes, fabrics, or paper.

14. The respiration monitor of claim 10, further comprising a voltage source configured to apply a voltage across the electrode pair.

15. The respiration monitor of claim 14, wherein the voltage source is a battery.

16. The respiration monitor of claim 10, further comprising a microcontroller for measuring a change in one or more of current, electrical resistance, voltage, or conductance.

17. The respiration monitor of claim 16, further comprising a wireless transmitter for transmission of meter data to a remote location.

18. The respiration monitor of claim 10, further comprising a sensitizing agent in or on the hygroscopic porous cellulose paper material.

* * * * *